United States Patent
Favre et al.

(10) Patent No.: US 11,274,102 B2
(45) Date of Patent: Mar. 15, 2022

(54) COMPOUNDS USEFUL IN HIV THERAPY

(71) Applicant: GLAXOSMITHKLINE INTELLECTUAL PROPERTY DEVELOPMENT LIMITED, Middlesex (GB)

(72) Inventors: David Favre, Research Triangle Park, NC (US); Robert G. Ferris, Research Triangle Park, NC (US); Jun Tang, Research Triangle Park, NC (US)

(73) Assignee: GLAXOSMITHKLINE INTELLECTUAL PROPERTY DEVELOPMENT LIMITED, Brentford (GB)

(*) Notice: Subject to any disclaimer, the term of this patent is extended or adjusted under 35 U.S.C. 154(b) by 141 days.

(21) Appl. No.: 16/758,085

(22) PCT Filed: Oct. 24, 2018

(86) PCT No.: PCT/IB2018/058306
§ 371 (c)(1),
(2) Date: Apr. 22, 2020

(87) PCT Pub. No.: WO2019/087016
PCT Pub. Date: May 9, 2019

(65) Prior Publication Data
US 2020/0325147 A1    Oct. 15, 2020

Related U.S. Application Data

(60) Provisional application No. 62/578,576, filed on Oct. 30, 2017.

(51) Int. Cl.
*C07D 491/048* (2006.01)
*A61K 9/16* (2006.01)
*A61K 9/20* (2006.01)

(52) U.S. Cl.
CPC ............ *C07D 491/048* (2013.01); *A61K 9/16* (2013.01); *A61K 9/20* (2013.01)

(58) Field of Classification Search
CPC ......... C07D 491/048; A61K 9/16; A61K 9/20
USPC ...................................................... 514/260.1
See application file for complete search history.

(56) References Cited

FOREIGN PATENT DOCUMENTS

WO    20170114048 A1    4/2017

OTHER PUBLICATIONS

Database PubChem Compound; Database accession No. 17474828; Nov. 13, 2007; XP002787478, retrieved from NCBI.
Xing, et al., "Targeting HIV latency: pharmacologic strategies toward eradication." Drug Discovery Today; 2013; pp. 541-551; vol. 18(11-12).

*Primary Examiner* — Kristin A Vajda
(74) *Attorney, Agent, or Firm* — Robert J. Smith

(57) ABSTRACT

The invention relates to compounds of Formula (I), (II) or (III), salts thereof, pharmaceutical compositions thereof, as well as therapeutic methods of treatment and prevention.

18 Claims, 1 Drawing Sheet

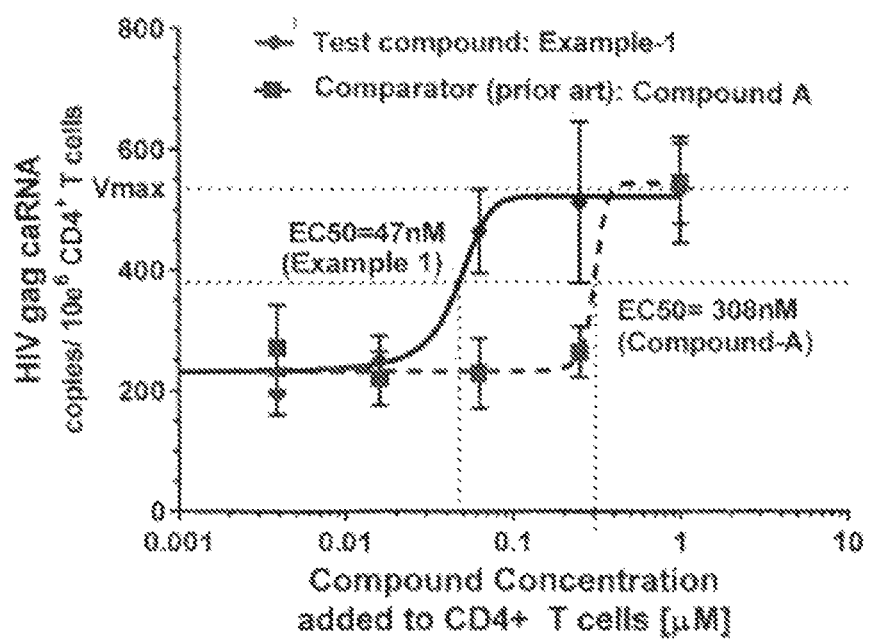
Dose-dependent HIV RNA Expression in total CD4+ T cells from HIV+ Donor

COMPOUNDS USEFUL IN HIV THERAPY

CROSS-REFERENCE TO RELATED APPLICATIONS

This application is filed pursuant to 35 U.S.C. § 371 as a United States National Phase Application of International Application No. PCT/IB2018/058306 filed Oct. 24, 2018 which claims priority from U.S. Provisional Application No. 62/578,576 filed Oct. 30, 2017.

FIELD OF THE INVENTION

The present invention relates to compounds, pharmaceutical compositions, and methods of use thereof in connection with individuals infected with HIV.

BACKGROUND OF THE INVENTION

Human immunodeficiency virus type 1 (HIV-1) infection leads to the contraction of acquired immune deficiency disease (AIDS). The number of cases of HIV continues to rise, and currently an estimated over thirty-five million individuals worldwide suffer from HIV infection e.g., http://www.sciencedirect.com/science/article/pii/S235230181630087X?_via%3Dihub Presently, long-term suppression of viral replication with antiretroviral drugs is the only option for treating HIV-1 infection. Indeed, the U.S. Food and Drug Administration has approved twenty-five drugs over six different inhibitor classes, which have been shown to greatly increase patient survival and quality of life. However, additional therapies are still believed to be required due to a number of issues including, but not limited to undesirable drug-drug interactions; drug-food interactions; non-adherence to therapy; drug resistance due to mutation of the enzyme target; and inflammation related to the immunologic damage caused by the HIV infection.

Currently, almost all HIV positive patients are treated with therapeutic regimens of antiretroviral drug combinations termed, highly active antiretroviral therapy ("HAART"). However, HAART therapies are often complex because a combination of different drugs must be administered often daily to the patient to avoid the rapid emergence of drug-resistant HIV-1 variants. Despite the positive impact of HAART on patient survival, drug resistance can still occur and the survival and quality of life are not normalized as compared to uninfected persons [Lohse Ann Intern Med 2007 146; 87-95]. Indeed, the incidence of several non-AIDS morbidities and mortalities, such as cardiovascular disease, frailty, and neurocognitive impairment, are increased in HAART-suppressed, HIV-infected subjects [Deeks Annu Rev Med 2011; 62:141-155]. This increased incidence of non-AIDS morbidity/mortality occurs in the context of, and is potentially caused by, elevated systemic inflammation related to the immunologic damage caused by HIV infection [Hunt J Infect Dis 2014][Byakagwa J Infect Dis 2014][Tenorio J Infect Dis 2014].

Modern antiretroviral therapy (ART) has the ability to effectively suppress HIV replication and improve health outcomes for HIV-infected persons, but is believed to not be capable of completely eliminating HIV viral reservoirs within the individual. HIV genomes can remain latent within mostly immune cells in the infected individual and may reactivate at any time, such that after interruption of ART, virus replication typically resumes within weeks. In a handful of individuals, the size of this viral reservoir has been significantly reduced and upon cessation of ART, the rebound of viral replication has been delayed [Henrich T J J Infect Dis 2013][Henrich T J Ann Intern Med 2014]. In one case, the viral reservoir was eliminated during treatment of leukemia and no viral rebound was observed during several years of follow-up [Nutter G N Engl J Med 2009]. These examples suggest the concept that reduction or elimination of the viral reservoir may be possible and can lead to viral remission or cure. As such, ways have been pursued to eliminate the viral reservoir, by direct molecular means, including excision of viral genomes with CRISPR/Cas9 systems, or to induce reactivation of the latent reservoir during ART so that the latent cells are eliminated. Induction of the latent reservoir typically results in either direct death of the latently infected cell or killing of the induced cell by the immune system after the virus is made visible. As this is performed during ART, viral genomes produced are believed to not result in the infection of new cells and the size of the reservoir may decay.

Reactivation of latent HIV is believed to be achieved by several means, typically by broad and potent mechanisms of cellular activation and enhancement of anti-HIV immunity. These reactivators and immune-modulators can be specific to certain cell types, such as anti-CD3/anti-CD28 antibodies that will specifically target T cells, or can be non-specific, such as protein kinase C (PKC) agonists that can activate many cell types. The immune-modulatory activities or immune enhancement of innate and adaptive anti-HIV immune responses may depend and vary upon the mechanism of action and level of target engagement.

Notwithstanding the above, there remains a need for compounds which may possess a desirable combination of potency, limited cytotoxicity, immune-modulation and chemical properties for development as a therapy for HIV.

SUMMARY OF THE INVENTION

In one aspect, the invention provides a compound of the formula (I):

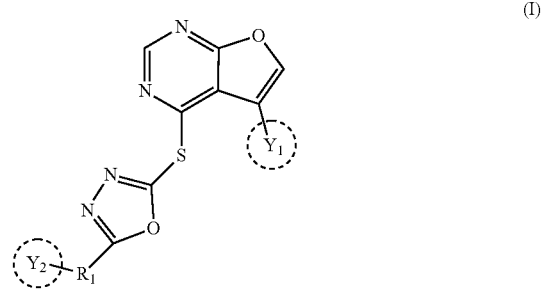

wherein:
$Y_1$ is a 5- or 6-membered aryl or heteroaryl optionally substituted by one or more substituents independently selected from the group consisting of chloro, fluoro, oxo, and alkoxy;
$R_1$ is $C_1$-$C_6$ alkylene; and
$Y_2$ is a ring of the formula:

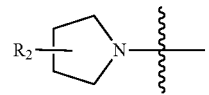

wherein $R_2$ is selected from the group consisting of -chloro, fluoro, oxo and alkoxy;

or a pharmaceutically acceptable salt thereof.

In another aspect, the invention provides pharmaceutical compositions comprising a compound of Formula (I) or a pharmaceutically acceptable salt thereof and an excipient In another aspect, the invention provides a method of treating, preventing or curing an HIV infection in a subject at risk for developing an HIV infection, comprising administering to the subject a compound of Formula (I), or a pharmaceutically acceptable salt thereof.

In another aspect, there is provided a compound of Formula (I) or a pharmaceutically acceptable salt thereof for use in therapy.

In another aspect, there is provided a compound of Formula (I) or a pharmaceutically acceptable salt thereof for use in treating, preventing or curing HIV infection.

In another aspect, there is provided the use of a compound of Formula (I) or a pharmaceutically acceptable salt thereof in the manufacture of a medicament for treating, preventing or curing HIV infection.

These and other aspects are encompassed by the invention as set forth herein.

BRIEF DESCRIPTION OF THE DRAWINGS

FIG. 1: represents the dose-response HIV latency disruption in CD4+ T cells from a fully-suppressed HIV-infected individual comparing compound of invention (Example-1) to Compound-A.

DETAILED DESCRIPTION OF REPRESENTATIVE EMBODIMENTS

Throughout this application, references are made to various embodiments relating to compounds, compositions, and methods. The various embodiments described are meant to provide a variety of illustrative examples and should not be construed as descriptions of alternative species. Rather it should be noted that the descriptions of various embodiments provided herein may be of overlapping scope. The embodiments discussed herein are merely illustrative and are not meant to limit the scope of the present invention. It is to be understood that the terminology used herein is for the purpose of describing particular embodiments only and is not intended to limit the scope of the present invention. In this specification and in the claims that follow, reference will be made to a number of terms that shall be defined to have the following meanings.

As used herein unless otherwise specified, "alkyl" refers to a monovalent saturated aliphatic hydrocarbyl group having from 1 to 14 carbon atoms and, in some embodiments, from 1 to 6 carbon atoms. "$(C_x$-$C_y)$alkyl" refers to alkyl groups having from x to y carbon atoms. The term "alkyl" includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkylene" or "alkylene" refers to divalent saturated aliphatic hydrocarbyl groups having from 1 to 6 carbon atoms. The alkylene groups include branched and straight chain hydrocarbyl groups. For example, "$(C_1$-$C_6)$alkylene" is meant to include methylene, ethylene, propylene, 2-methypropylene, dimethylethylene, pentylene, and so forth. As such, the term "propylene" could be exemplified by the following structure:

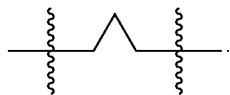 [SMILES: *CCC*]

Likewise, the term "dimethylbutylene" could be exemplified by any of the following three structures or more:

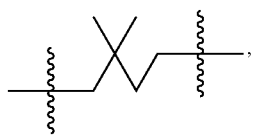 [SMILES: *CCC(C)(C)C*]

p, or

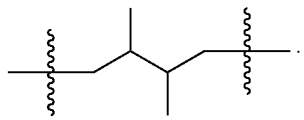 [SMILES: *CC(C)C(C)C*]

Furthermore, the term "$(C_1$-$C_6)$alkylene" is meant to include such branched chain hydrocarbyl groups as cyclopropylmethylene, which could be exemplified by the following structure:

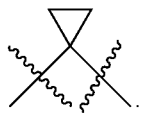

Alkoxy" refers to the group —O-alkyl wherein alkyl is defined herein, e.g., $C_1$ to $C_6$ alkoxy. Alkoxy includes, by way of example, methoxy, ethoxy, n-propoxy, isopropoxy, n-butoxy, t-butoxy, sec-butoxy, and n-pentoxy.

".

"Aryl" refers to an aromatic group of from 5 to 6 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"AUC" refers to the area under the plot of plasma concentration of drug (not logarithm of the concentration) against time after drug administration.

"$EC_{50}$" refers to the concentration of a drug that gives half-maximal response.

"$IC_{50}$" refers to the half-maximal inhibitory concentration of a drug. Sometimes, it is also converted to the $pIC_{50}$ scale (–log $IC_{50}$), in which higher values indicate exponentially greater potency.

"Heteroaryl" refers to an aromatic group of from 1 to 14 carbon atoms, e.g., 5 to 6 heteroatoms selected from oxygen, nitrogen, and sulfur and includes single ring (e.g. imidazolyl) and (e.g. benzimidazol-2-yl and benzimidazol-6-yl). For multiple ring systems, including fused, bridged, and spiro ring systems having aromatic and non-aromatic rings, the term "heteroaryl" applies if there is at least one ring heteroatom and the point of attachment is at an atom of an aromatic ring (e.g. 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. More specifically the term heteroaryl includes, but is not limited to, pyridyl, furanyl, thienyl, thiazolyl, isothiazolyl, triazolyl, imidazolyl, imidazolinyl, isoxazolyl, pyrrolyl, pyrazolyl, pyridazinyl, pyrimidinyl, purinyl, phthalazyl, naphthylpryidyl, benzofuranyl, tetrahydrobenzofuranyl, isobenzofuranyl, benzothiazolyl, benzoisothiazolyl, benzotriazolyl, indolyl, isoindolyl, indolizinyl, dihydroindolyl, indazolyl, indolinyl, benzoxazolyl, quinolyl, isoquinolyl, quinolizyl, quianazolyl, quinoxalyl, tetrahydroquinolinyl, isoquinolyl, quinazolinonyl, benzimidazolyl, benzisoxazolyl, benzothienyl, benzopyridazinyl, pteridinyl, carbazolyl, carbolinyl, phenanthridinyl, acridinyl, phenanthrolinyl, phenazinyl, phenoxazinyl, phenothiazinyl, and phthalimidyl.

Examples of heteroaryl groups include, but are not limited to, azetidine, pyrrole, imidazole, pyrazole, pyridine, pyrazine, pyrimidine, pyridazine, pyridone, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholine, thiomorpholine (also referred to as thiamorpholine), piperidine, pyrrolidine, and tetrahydrofuranyl.

"Compound", "compounds", "chemical entity", and "chemical entities" as used herein refers to a compound encompassed by the generic formulae disclosed herein, any subgenus of those generic formulae, and any forms of the compounds within the generic and subgeneric formulae, including the racemates, stereoisomers, and tautomers of the compound or compounds.

The term "heteroatom" means nitrogen, oxygen, or sulfur and includes any oxidized form of nitrogen, such as N(O) {$N^+$—$O^-$} and sulfur such as S(O) and S(O)$_2$, and the quaternized form of any basic nitrogen.

"Oxo" refers to a (=O) group.

"Polymorphism" refers to when two or more clearly different phenotypes exist in the same population of a species where the occurrence of more than one form or morph. In order to be classified as such, morphs must occupy the same habitat at the same time and belong to a panmictic population (one with random mating).

"Protein binding" refers to the binding of a drug to proteins in blood plasma, tissue membranes, red blood cells and other components of blood.

"Protein shift" refers to determining a binding shift by comparing the $EC_{50}$ values determined in the absence and presence of human serum.

"Racemates" refers to a mixture of enantiomers. In an embodiment of the invention, the compounds of Formulas I, II and III or pharmaceutically acceptable salts thereof, are enantiomerically enriched with one enantiomer wherein all of the chiral carbons referred to are in one configuration. In general, reference to an enantiomerically enriched compound or salt, is meant to indicate that the specified enantiomer will comprise more than 50% by weight of the total weight of all enantiomers of the compound or salt.

"Solvate" or "solvates" of a compound refer to those compounds, as defined above, which are bound to a stoichiometric or non-stoichiometric amount of a solvent. Solvates of a compound includes solvates of all forms of the compound. In certain embodiments, solvents are volatile, non-toxic, and/or acceptable for administration to humans in trace amounts. Suitable solvates include water.

"Stereoisomer" or "stereoisomers" refer to compounds that differ in the chirality of one or more stereocenters. Stereoisomers include enantiomers and diastereomers.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

The term 'atropisomer' refers to a stereoisomer resulting from an axis of asymmetry. This can result from restricted rotation about a single bond where the rotational barrier is high enough to allow differentiation of the isomeric species up to and including complete isolation of stable non-interconverting diastereomer or enantiomeric species. One skilled in the art will recognize that upon installing a nonsymmetrical $R^x$ to core, the formation of atropisomers is possible. In addition, once a second chiral center is installed in a given molecule containing an atropisomer, the two chiral elements taken together can create diastereomeric and enantiomeric stereochemical species. Depending upon the substitution about the Cx axis, interconversion between the atropisomers may or may not be possible and may depend on temperature. In some instances, the atropisomers may interconvert rapidly at room temperature and not resolve under ambient conditions. Other situations may allow for resolution and isolation but interconversion can occur over a period of seconds to hours or even days or months such that optical purity is degraded measurably over time. Yet other species may be completely restricted from interconversion under ambient and/or elevated temperatures such that resolution and isolation is possible and yields stable species. When known, the resolved atropisomers were named using the helical nomenclature. For this designation, only the two ligands of highest priority in front and behind the axis are considered. When the turn priority from the front ligand 1 to the rear ligand 1 is clockwise, the configuration is P, if counterclockwise it is M.

"Pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

"Patient" or "subject" refers to mammals and includes humans and non-human mammals.

"Cure" or "Curing" a disease in a patient refer to is used to the denote the eradication, stoppage, halt or end of the human immunodeficiency virus or symptoms, or the progression of the symptoms or virus, for a defined period. As an example, in one embodiment, "cure" or "curing" refers to a therapeutic administration or a combination of administrations that alone or in combination with one or more other compounds induces and maintains sustained viral control (undetectable levels of plasma viremia by, e.g., a polymerase chain reaction (PCR) test, a bDNA (branched chain DNA) test or a NASBA (nucleic acid sequence based amplification) test) of human immunodeficiency virus after a minimum of two years without any other therapeutic intervention. The above PCR, bDNA and NASBA tests are carried out using techniques known and familiar to one skilled in the art. As an example, the eradication, stoppage, halt or end of the human immunodeficiency virus or symptoms, or the progression of the symptoms or virus, may be sustained for a minimum of two years.

Treating" or "treatment" of a disease in a patient refers to 1) preventing the disease from occurring in a patient that is predisposed or does not yet display symptoms of the disease; 2) inhibiting the disease or arresting its development; or 3) ameliorating or causing regression of the disease.

Where specific compounds or generic formulas are drawn that have aromatic rings, such as aryl or heteroaryl rings, then it will be understood by one of still in the art that the particular aromatic location of any double bonds are a blend of equivalent positions even if they are drawn in different locations from compound to compound or from formula to formula. For example, in the two pyridine rings (A and B) below, the double bonds are drawn in different locations, however, they are known to be the same structure and compound:

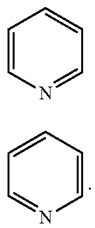

A

B

The present invention includes compounds as well as their pharmaceutically acceptable salts. Accordingly, the word "or" in the context of "a compound or a pharmaceutically acceptable salt thereof" is understood to refer to either: 1) a compound alone or a compound and a pharmaceutically acceptable salt thereof (alternative), or 2) a compound and a pharmaceutically acceptable salt thereof (in combination).

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—. In a term such as "—C(R$^x$)$_2$", it should be understood that the two R$^x$ groups can be the same, or they can be different if R$^x$ is defined as having more than one possible identity. In addition, certain substituents are drawn as —R$^x$R$^y$, where the "-" indicates a bond adjacent to the parent molecule and R$^y$ being the terminal portion of the functionality. Similarly, it is understood that the above definitions are not intended to include impermissible substitution patterns (e.g., methyl substituted with 5 fluoro groups). Such impermissible substitution patterns are well known to the skilled artisan.

In one aspect, there is provided a compound of the formula (I):

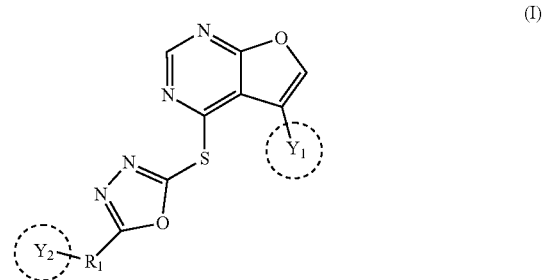

(I)

wherein:

Y$_1$ is a 5- or 6-membered aryl or heteroaryl optionally substituted by one or more substituents independently selected from the group consisting of chloro, fluoro, oxo, and alkoxy;

R$_1$ is C$_1$-C$_6$ alkylene; and

Y$_2$ is a ring of the formula:

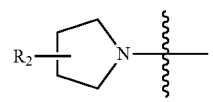

wherein R$_2$ is selected from the group consisting of -chloro, fluoro, oxo and alkoxy; or a pharmaceutically acceptable salt thereof.

In one embodiment of the present invention, there is provided a compound of formula (I) wherein Y$_1$ is an aryl.

In one embodiment of the present invention, there is provided a compound of formula (I) wherein Y$_1$ is an aryl substituted by Cl.

In one embodiment of the present invention, there is provided a compound of formula (I), wherein Y$_1$ is of the formula:

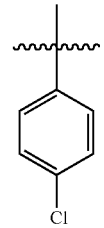

In one embodiment of the present invention, there is provided a compound of formula (I) wherein Y$_1$ is a 5-membered heteroaryl.

In one embodiment of the present invention, there is provided a compound of formula (I) wherein the 5-membered heteroaryl contains at least one heteroatom which is O or S.

In one embodiment of the present invention, there is provided a compound of formula (I), wherein R$_1$ is C$_1$ alkyl.

In one embodiment of the present invention, there is provided a compound of formula (I) wherein R$_1$ is C$_2$ alkyl.

In one embodiment of the present invention, there is provided a compound of formula (I) wherein R$_2$ is oxo.

In one embodiment of the present invention, there is provided a compound of formula (I), selected from the group consisting of:

TABLE 1

| Parent Structure | Chemical Name |
| --- | --- |
|  | 1-((5-((5-(4-chlorophenyl)furo[2,3-d]pyrimidin-4-yl)thio)-1,3,4-oxadiazol-2-yl)methyl)pyrrolidin-2-one |
|  | 1-((5-((5-(4-chlorophenyl)furo[2,3-d]pyrimidin-4-yl)thio)-1,3,4-oxadiazol-2-yl)methyl)pyrrolidin-2-one |
|  | 1-((5-((5-(4-chlorophenyl)furo[2,3-d]pyrimidin-4-yl)thio)-1,3,4-oxadiazol-2-yl)methyl)pyrrolidin-2-one |
|  | 1-((5-((5-(furan-2-yl)furo[2,3-d]pyrimidin-4-yl)thio)-1,3,4-oxadiazol-2-yl)methyl)pyrrolidin-2-one |

TABLE 1-continued

| Parent Structure | Chemical Name |
|---|---|
|  | 1-((5-((5-(furan-2-yl)furo[2,3-d]pyrimidin-4-yl)thio)-1,3,4-oxadiazol-2-yl)methyl)pyrrolidin-2-one |
|  | 1-((5-((5-(thiophen-2-yl)furo[2,3-d]pyrimidin-4-yl)thio)-1,3,4-oxadiazol-2-yl)methyl)pyrrolidin-2-one |
|  | 1-((5-((5-(5-methylthiophen-2-yl)furo[2,3-d]pyrimidin-4-yl)thio)-1,3,4-oxadiazol-2-yl)methyl)pyrrolidin-2-one | and a pharmaceutically acceptable salt thereof.

In one embodiment, the present invention encompasses each individual compound listed in the above Table 1, or a pharmaceutically acceptable salt thereof.

In one embodiment of the present invention, there is provided a compound of formula (II):

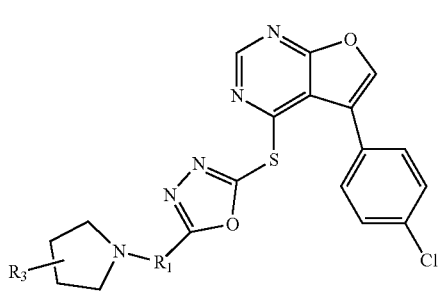

(II)

wherein $R_1$ is $C_1$-$C_6$ alkyl; and
$R_3$ is hydrogen, oxo, chloro or fluoro.

In one embodiment of the present invention, there is provided a compound of formula (III):

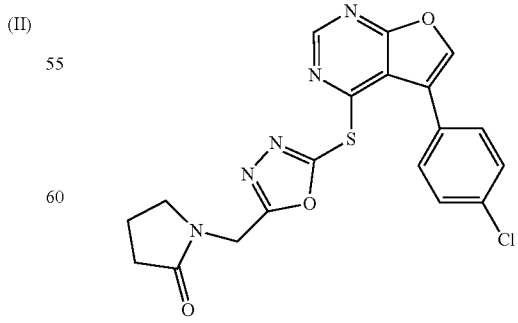

(III)

or a pharmaceutically acceptable salt thereof.

In accordance with one embodiment of the present invention, there is provided a pharmaceutical composition comprising a compound of Formula (I), (II) or (III) or a pharmaceutically acceptable salt thereof, and a pharmaceutically acceptable excipient. In a further embodiment, the compound is present in amorphous form. In a further embodiment, the pharmaceutical composition is in a tablet form. In a further embodiment, the compound is present as a spray dried dispersion.

In accordance with one embodiment of the present invention, there is provided a method of curing an HIV infection in a subject comprising administering to the subject a compound of Formula (I), (II) or (III) or a pharmaceutically acceptable salt thereof.

In accordance with one embodiment of the present invention, there is provided a method of curing an HIV infection in a subject comprising administering to the subject a pharmaceutical composition as described herein.

In accordance with one embodiment of the present invention, there is provided a method of treating an HIV infection in a subject comprising administering to the subject a compound of Formula (I), (II) or (III) a pharmaceutically acceptable salt thereof.

In accordance with one embodiment of the present invention, there is provided a method of treating an HIV infection in a subject comprising administering to the subject a pharmaceutical composition as described herein.

In accordance with one embodiment of the present invention, there is provided a method of preventing an HIV infection in a subject at risk for developing an HIV infection, comprising administering to the subject a compound of Formula (I), (II) or (III) or a pharmaceutically acceptable salt thereof.

In accordance with one embodiment of the present invention, there is provided the use of a compound of Formula (I), (II) or (III), in the manufacture of a medicament for curing an HIV infection.

In accordance with one embodiment of the present invention, there is provided the use of a compound of Formula (I), (II) or (III), in the manufacture of a medicament for treating an HIV infection.

In accordance with one embodiment of the present invention, there is provided the use of a compound of Formula (I), (II) or (III), in the manufacture of a medicament for preventing an HIV infection.

In accordance with one embodiment of the present invention, there is provided a compound according to Formula (I), (II), or (III), for use in curing an HIV infection.

In accordance with one embodiment of the present invention, there is provided a compound according to Formula (I), (II), or (III), for use in treating an HIV infection.

In accordance with one embodiment of the present invention, there is provided a compound according to Formula (I), (II), or (III), for use in preventing an HIV infection.

In accordance with one embodiment of the present invention, there is provided a method of preventing an HIV infection in a subject at risk for developing an HIV infection, comprising administering to the subject a pharmaceutical composition as described herein.

Furthermore, the compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

In another embodiment of the invention, there is provided a compound of Formula (I), (II) or (III), wherein the compound or salt of the compound is used in the manufacture of a medicament for use in the treatment of an HIV infection in a human.

In another embodiment of the invention, there is provided a compound of Formula (I), (II) or (III) wherein the compound or salt of the compound is used in the manufacture of a medicament for use in the prevention of an HIV infection in a human.

In another embodiment of the invention, there is provided a compound of Formula (I), (II) or (III), wherein the compound or salt of the compound is used in the manufacture of a medicament for use in the cure of an HIV infection in a human.

In one embodiment, the pharmaceutical formulation containing a compound of Formula (I), (II) or (III) or a salt thereof is a formulation adapted for parenteral administration. In another embodiment, the formulation is a long-acting parenteral formulation. In a further embodiment, the formulation is a nano-particle formulation.

The compounds of the present invention and their salts, solvates, or other pharmaceutically acceptable derivatives thereof, may be employed alone or in combination with other therapeutic agents. Therefore, in other embodiments, the methods of treating and/or preventing an HIV infection in a subject may in addition to administration of a compound of Formula (I), (II) or (III) further comprise administration of one or more additional pharmaceutical agents active against HIV.

In such embodiments, the one or more additional agents active against HIV is selected from the group consisting of zidovudine, didanosine, lamivudine, zalcitabine, abacavir, stavudine, adefovir, adefovir dipivoxil, fozivudine, todoxil, emtricitabine, alovudine, amdoxovir, elvucitabine, nevirapine, delavirdine, efavirenz, loviride, immunocal, oltipraz, capravirine, lersivirine, GSK2248761, TMC-278, TMC-125, etravirine, saquinavir, ritonavir, indinavir, nelfinavir, amprenavir, fosamprenavir, brecanavir, darunavir, atazanavir, tipranavir, palinavir, lasinavir, enfuvirtide, T-20, T-1249, PRO-542, PRO-140, TNX-355, BMS-806, BMS-663068 and BMS-626529, 5-Helix, raltegravir, elvitegravir, dolutegravir, cabotegravir, vicriviroc (Sch-C), Sch-D, TAK779, maraviroc, TAK449, didanosine, tenofovir, lopinavir, and darunavir.

As such, the compounds of the present invention of Formula (I), (II) or (III) and any other pharmaceutically active agent(s) may be administered together or separately and, when administered separately, administration may occur simultaneously or sequentially, in any order. The amounts of the compounds of Formula (I), (II) or (III) of the present invention and the other pharmaceutically active agent(s) and the relative timings of administration will be selected in order to achieve the desired combined therapeutic effect. The administration in combination of a compound of the present invention of Formula (I), (II) or (III) and salts, solvates, or other pharmaceutically acceptable derivatives thereof with other treatment agents may be in combination by administration concomitantly in: (1) a unitary pharmaceutical composition including both compounds; or (2) separate pharmaceutical compositions each including one of the compounds. Alternatively, the combination may be administered separately in a sequential manner wherein one treatment agent is administered first and the other second or vice versa. Such sequential administration may be close in time or remote in time. The amounts of the compound(s) of Formula (I), (II) or (III) or salts thereof and the other pharmaceutically active agent(s) and the relative timings of administration will be selected in order to achieve the desired combined therapeutic effect.

In addition, the compounds of the present invention of Formula (I), (II) or (III) may be used in combination with one or more other agents that may be useful in the prevention, treatment or cure of HIV. Examples of such agents include:

Nucleotide reverse transcriptase inhibitors such as zidovudine, didanosine, lamivudine, zalcitabine, abacavir, stavudine, adefovir, adefovir dipivoxil, fozivudine, todoxil, emtricitabine, alovudine, amdoxovir, elvucitabine, and similar agents;

Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, lersivirine, GSK2248761, TMC-278, TMC-125, etravirine, and similar agents;

Protease inhibitors such as saquinavir, ritonavir, indinavir, nelfinavir, amprenavir, fosamprenavir, brecanavir, darunavir, atazanavir, tipranavir, palinavir, lasinavir, and similar agents;

Entry, attachment and fusion inhibitors such as enfuvirtide (T-20), T-1249, PRO-542, PRO-140, TNX-355, BMS-806, BMS-663068, BMS-626529, 5-Helix and similar agents;

Integrase inhibitors such as raltegravir, elvitegravir, dolutegravir, bictegravir, cabotegravir and similar agents;

Maturation inhibitors such as PA-344 and PA-457, and similar agents; and

CXCR4 and/or CCR5 inhibitors such as vicriviroc (Sch-C), Sch-D, TAK779, maraviroc (UK 427,857), TAK449, as well as those disclosed in WO 02/74769, PCT/US03/39644, PCT/US03/39975, PCT/US03/39619, PCT/US03/39618, PCT/US03/39740, and PCT/US03/39732, and similar agents.

Further examples where the compounds of the present invention may be used in combination with one or more agents useful in the prevention or treatment of HIV are found in Table 2.

TABLE 2

| FDA Approval | Brand Name | Generic Name | Manufacturer |
|---|---|---|---|
| Nucleoside Reverse Transcriptase Inhibitors (NRTIs) | | | |
| 1987 | Retrovir | zidovudine, azidothymidine, AZT, ZDV | GlaxoSmithKline |
| 1991 | Videx | didanosine, dideoxyinosine, ddI | Bristol-Myers Squibb |
| 1992 | Hivid | zalcitabine, dideoxycytidine, ddC | Roche Pharmaceuticals |
| 1994 | Zerit | stavudine, d4T | Bristol-Myers Squibb |
| 1995 | Epivir | lamivudine, 3TC | GlaxoSmithKline |
| 1997 | Combivir | lamivudine + zidovudine | GlaxoSmithKline |
| 1998 | Ziagen | abacavir sulfate, ABC | GlaxoSmithKline |
| 2000 | Trizivir | abacavir + lamivudine + zidovudine | GlaxoSmithKline |
| 2000 | Videx EC | enteric coated didanosine, ddI EC | Bristol-Myers Squibb |
| 2001 | Viread | tenofovir disoproxil fumarate, TDF | Gilead Sciences |
| 2003 | Emtriva | emtricitabine, FTC | Gilead Sciences |
| 2004 | Epzicom | abacavir + lamivudine | GlaxoSmithKline |
| 2004 | Truvada | emtricitabine + tenofovir disoproxil fumarate | Gilead Sciences |
| Non-Nucleosides Reverse Transcriptase Inhibitors (NNRTIs) | | | |
| 1996 | Viramune | nevirapine, NVP | Boehringer Ingelheim |
| 1997 | Rescriptor | delavirdine, DLV | Pfizer |
| 1998 | Sustiva | efavirenz, EFV | Bristol-Myers Squibb |
| 2008 | Intelence | Etravirine | Tibotec Therapeutics |
| Protease Inhibitors (PIs) | | | |
| 1995 | Invirase | saquinavir mesylate, SQV | Roche Pharmaceuticals |
| 1996 | Norvir | ritonavir, RTV | Abbott Laboratories |
| 1996 | Crixivan | indinavir, IDV | Merck |
| 1997 | Viracept | nelfinavir mesylate, NFV | Pfizer |
| 1997 | Fortovase | saquinavir (no longer marketed) | Roche Pharmaceuticals |
| 1999 | Agenerase | amprenavir, APV | GlaxoSmithKline |
| 2000 | Kaletra | lopinavir + ritonavir, LPV/RTV | Abbott Laboratories |
| 2003 | Reyataz | atazanavir sulfate, ATV | Bristol-Myers Squibb |
| 2003 | Lexiva | fosamprenavir calcium, FOS-APV | GlaxoSmithKline |
| 2005 | Aptivus | tripranavir, TPV | Boehringer Ingelheim |
| 2006 | Prezista | Darunavir | Tibotec Therapeutics |
| Fusion Inhibitors | | | |
| 2003 | Fuzeon | Enfuvirtide, T-20 | Roche Pharmaceuticals & Trimeris |
| Entry Inhibitors | | | |
| 2007 | Selzentry | Maraviroc | Pfizer |
| Integrase Inhibitors | | | |
| 2007 | Isentress | Raltegravir | Merck |
| 2013 | Tivicay | Dolutegravir | ViiV Healthcare |
| — | — | Cabotegravir | |

The scope of combinations of compounds of this invention with HIV agents is not limited to those mentioned above, but includes in principle any combination with any pharmaceutical composition useful for the cure, treatment and/or prevention of HIV. As noted, in such combinations the compounds of the present invention and other HIV agents may be administered separately or in conjunction. In addition, one agent may be prior to, concurrent to, or subsequent to the administration of other agent(s).

The present invention may be used in combination with one or more agents useful as pharmacological enhancers as well as with or without additional compounds for the prevention or treatment of HIV. Examples of such pharmacological enhancers (or pharmakinetic boosters) include, but are not limited to, ritonavir, GS-9350, and SPI-452. Ritonavir is 10-hydroxy-2-methyl-5-(1-methyethyl)-1-1[2-(1-methylethyl)-4-thiazolyl]-3,6-dioxo-8,11-bis(phenylmethyl)-2,4,7,12-tetraazatridecan-13-oic acid, 5-thiazolylmethyl ester, [5S-(5S*,8R*,10R*,11R*)] and is available from Abbott Laboratories of Abbott park, Illinois, as Norvir. Ritonavir is an HIV protease inhibitor indicated with other antiretroviral agents for the treatment of HIV infection. Ritonavir also inhibits P450 mediated drug metabolism as well as the P-gycoprotein (Pgp) cell transport system, thereby resulting in increased concentrations of active compound within the organism.

GS-9350 is a compound being developed by Gilead Sciences of Foster City Calif. as a pharmacological enhancer. SPI-452 is a compound being developed by *Sequoia* Pharmaceuticals of Gaithersburg, Md., as a pharmacological enhancer.

In one embodiment of the present invention, a compound of Formula (I), (II) or (III) is used in combination with ritonavir. In one embodiment, the combination is an oral fixed dose combination. In another embodiment, the compound of Formula (I), (II) or (III) is formulated as a long acting parenteral injection and ritonavir is formulated as an oral composition. In one embodiment, a kit containing the compound of Formula (I), (II), or (III) is formulated as a long acting parenteral injection and ritonavir formulated as an oral composition. In another embodiment, the compound of Formula (I), (II) or (III) is formulated as a long acting parenteral injection and ritonavir is formulated as an injectable composition. In one embodiment, a kit containing the compound of Formula (I), (II) or (III) is formulated as a long acting parenteral injection and ritonavir formulated as an injectable composition.

In another embodiment of the present invention, a compound of Formula (I), (II), or (III) is used in combination with GS-9350. In one embodiment, the combination is an oral fixed dose combination. In another embodiment, the compound of Formula (I), (II) or (III) is formulated as a long acting parenteral injection and GS-9350 is formulated as an oral composition. In one embodiment, there is provided a kit containing the compound of Formula (I), (II) or (III) formulated as a long acting parenteral injection and GS-9350 formulated as an oral composition. In another embodiment, the compound of Formula (I), (II) or (III) is formulated as a long acting parenteral injection and GS-9350 is formulated as an injectable composition. In one embodiment, is a kit containing the compound of Formula (I), (II) or (III) is formulated as a long acting parenteral injection and GS-9350 formulated as an injectable composition.

In one embodiment of the present invention, a compound of Formula (I), (II) or (III) is used in combination with SPI-452. In one embodiment, the combination is an oral fixed dose combination. In another embodiment, the compound of Formula (I), (II) or (III) is formulated as a long acting parenteral injection and SPI-452 is formulated as an oral composition. In one embodiment, there is provided a kit containing the compound of Formula (I), (II) or (III) formulated as a long acting parenteral injection and SPI-452 formulated as an oral composition. In another embodiment, the compound of Formula (I), (II) or (III) is formulated as a long acting parenteral injection and SPI-452 is formulated as an injectable composition. In one embodiment, there is provided a kit containing the compound of Formula (I), (II) or (III) formulated as a long acting parenteral injection and SPI-452 formulated as an injectable composition.

In one embodiment of the present invention, a compound of Formula (I), (II) or (III) is used in combination with compounds which are found in previously filed PCT/CN2011/0013021, which is herein incorporated by reference.

The above other therapeutic agents, when employed in combination with the chemical entities described herein, may be used, for example, in those amounts indicated in the Physicians' Desk Reference (PDR) or as otherwise determined by one of ordinary skill in the art.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III).

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III), wherein said virus is an HIV virus. In some embodiments, the HIV virus is the HIV-1 virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III) further comprising administration of a therapeutically effective amount of one or more agents active against an HIV virus.

In another embodiment of the invention, there is provided a method for treating a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III), further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III).

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III), wherein said virus is an HIV virus. In some embodiments, the HIV virus is the HIV-1 virus.

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III), further comprising administration of a therapeutically effective amount of one or more agents active against an HIV virus.

In another embodiment of the invention, there is provided a method for preventing a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III), further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In another embodiment of the invention, there is provided a method for curing a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III).

In another embodiment of the invention, there is provided a method for curing a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III), wherein said virus is an HIV virus. In some embodiments, the HIV virus is the HIV-1 virus.

In another embodiment of the invention, there is provided a method for curing a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III), further comprising administration of a therapeutically effective amount of one or more agents active against an HIV virus.

In another embodiment of the invention, there is provided a method for curing a viral infection in a mammal mediated at least in part by a virus in the retrovirus family of viruses which method comprises administering to a mammal, that has been diagnosed with said viral infection or is at risk of developing said viral infection, a compound of Formula (I), (II) or (III) further comprising administration of a therapeutically effective amount of one or more agents active against the HIV virus, wherein said agent active against HIV virus is selected from Nucleotide reverse transcriptase inhibitors; Non-nucleotide reverse transcriptase inhibitors; Protease inhibitors; Entry, attachment and fusion inhibitors; Integrase inhibitors; Maturation inhibitors; CXCR4 inhibitors; and CCR5 inhibitors.

In various embodiments, the compounds of the present invention of Formula (I), (II) or (III), or a pharmaceutically acceptable salt thereof, may be used in treating cancer in a subject comprising administering to the subject a compound of the present invention, pharmaceutically acceptable salt thereof. Combinations of compounds, as well as pharmaceutical compositions of all of the above, are encompasses in such methods of treatment. As used in the context of these methods of treatment, the term "treatment" or "treating" in the context of therapeutic methods, refers to alleviating the specified condition, eliminating or reducing the symptoms of the condition, slowing or eliminating the progression, invasion, or metastatic spread of the condition and preventing or delaying the reoccurrence of the condition in a previously afflicted subject. The present invention further provides use of the compounds of the invention, pharmaceutically acceptable salts thereof, as well as pharmaceutical compositions thereof, as well as for the preparation of a medicament for the treatment of cancer in a mammal (e.g., human) in need thereof. Cancers that may be treated include, without limitation, brain (gliomas), breast cancer, inflammatory breast cancer, colorectal cancer, Wilm's tumor, Ewing's sarcoma, Rhabdomyosarcoma, ependymoma, medulloblastoma, colon cancer, head and neck cancer, kidney cancer, lung cancer, liver cancer, melanoma, squamous cell carcinoma, ovarian cancer, pancreatic cancer, prostate cancer, sarcoma cancer, osteosarcoma, giant cell tumor of bone, thyroid cancer, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, Plasmacytoma, Immunoblastic large cell leukemia, Mantle cell leukemia, Multiple myeloma, Megakaryoblastic leukemia, multiple myeloma, Acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor), and testicular cancer.

In further embodiments, the compound of the present invention of Formula (I), (II) or (III) or a pharmaceutically acceptable salt thereof, is selected from the group of compounds set forth in Table 1 above.

The compounds of Table 1 were synthesized according to the Synthetic Methods, General Schemes, and the Examples described below.

In another embodiment, there is provided a pharmaceutical composition comprising a pharmaceutically acceptable diluent and a therapeutically effective amount of a compound of Formula (I), (II) and (III) or a pharmaceutically acceptable salt thereof.

In certain embodiments, the compound(s) of the present invention, or a pharmaceutically acceptable salt thereof, is chosen from the compounds set forth in Table 1. The compounds of the present invention can be supplied in the form of a pharmaceutically acceptable salt. The terms "pharmaceutically acceptable salt" refer to salts prepared from pharmaceutically acceptable inorganic and organic acids and bases. Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication. The skilled artisan will appreciate that pharmaceutically acceptable salts of compounds according to Formula (I), (II) or (III) may be prepared. These pharmaceutically acceptable salts may be prepared in situ during the final isolation and purification of the compound, or by separately reacting the purified compound in its free acid or free base form with a suitable base or acid, respectively.

Illustrative pharmaceutically acceptable acid salts of the compounds of the present invention can be prepared from the following acids, including, without limitation formic, acetic, propionic, benzoic, succinic, glycolic, gluconic, lactic, maleic, malic, tartaric, citric, nitic, ascorbic, glucuronic, maleic, fumaric, pyruvic, aspartic, glutamic, benzoic, hydrochloric, hydrobromic, hydroiodic, isocitric, trifluoroacetic, pamoic, propionic, anthranilic, mesylic, oxalacetic, oleic, stearic, salicylic, p-hydroxybenzoic, nicotinic, phenylacetic, mandelic, embonic (pamoic), methanesulfonic, phosphoric, phosphonic, ethanesulfonic, benzenesulfonic, pantothenic, toluenesulfonic, 2-hydroxyethanesulfonic, sulfanilic, sulfuric, salicylic, cyclohexylaminosulfonic, algenic, β-hydroxybutyric, galactaric and galacturonic acids. Preferred pharmaceutically acceptable salts include the salts of hydrochloric acid and trifluoroacetic acid.

Illustrative pharmaceutically acceptable inorganic base salts of the compounds of the present invention include metallic ions. More preferred metallic ions include, but are not limited to, appropriate alkali metal salts, alkaline earth metal salts and other physiological acceptable metal ions. Salts derived from inorganic bases include aluminum, ammonium, calcium, copper, ferric, ferrous, lithium, magnesium, manganic salts, manganous, potassium, sodium, zinc, and the like and in their usual valences. Exemplary base salts include aluminum, calcium, lithium, magnesium, potassium, sodium and zinc. Other exemplary base salts include the ammonium, calcium, magnesium, potassium, and sodium salts. Still other exemplary base salts include, for example, hydroxides, carbonates, hydrides, and alkoxides including NaOH, KOH, $Na_2CO_3$, $K_2CO_3$, NaH, and potassium-t-butoxide.

Salts derived from pharmaceutically acceptable organic non-toxic bases include salts of primary, secondary, and tertiary amines, including in part, trimethylamine, diethylamine, N, N'-dibenzylethylenediamine, chloroprocaine, choline, diethanolamine, ethylenediamine, meglumine (N-methylglucamine) and procaine; substituted amines including naturally occurring substituted amines; cyclic amines; quaternary ammonium cations; and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

All of the above salts can be prepared by those skilled in the art by conventional means from the corresponding compound of the present invention. For example, the pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. The salt may precipitate from solution and be collected by filtration or may be recovered by evaporation of the solvent. The degree of ionisation in the salt may vary from completely ionised to almost non-ionised. Lists of suitable salts are found in *Remington's Pharmaceutical Sciences,* 17th ed., Mack Publishing Company, Easton, Pa., 1985, p. 1418, the disclosure of which is hereby incorporated by reference only with regards to the lists of suitable salts.

The compounds of Formula (I), (II) or (III) of the invention may exist in both unsolvated and solvated forms. The term 'solvate' comprises the compound of the invention and one or more pharmaceutically acceptable solvent molecules, for example, ethanol. The term 'hydrate' is employed when said solvent is water. Pharmaceutically acceptable solvates include hydrates and other solvates wherein the solvent of crystallization may be isotopically substituted, e.g. $D_2O$, $d_6$-acetone, $d_6$-DMSO.

Compounds of Formula (I), (II) or (III) containing one or more asymmetric carbon atoms can exist as two or more stereoisomers. Where a compound of Formula (I), (II) or (III) contains an alkenyl or alkenylene group or a cycloalkyl group, geometric cis/trans (or Z/E) isomers are possible. Where the compound contains, for example, a keto or oxime group or an aromatic moiety, tautomeric isomerism ('tautomerism') can occur. It follows that a single compound may exhibit more than one type of isomerism.

Included within the scope of the claimed compounds present invention are all stereoisomers, geometric isomers and tautomeric forms of the compounds of Formula (I), (II) or (III), including compounds exhibiting more than one type of isomerism, and mixtures of one or more thereof. Also included are acid addition or base salts wherein the counterion is optically active, for example, D-lactate or L-lysine, or racemic, for example, DL-tartrate or DL-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of Formula (I), (II) or (III) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person. Chiral compounds of the invention (and chiral precursors thereof) may be obtained in enantiomerically-enriched form using chromatography, typically HPLC, on a resin with an asymmetric stationary phase and with a mobile phase consisting of a hydrocarbon, typically heptane or hexane, containing from 0 to 50% isopropanol, typically from 2 to 20%, and from 0 to 5% of an alkylamine, typically 0.1% diethylamine. Concentration of the eluate affords the enriched mixture.

Mixtures of stereoisomers may be separated by conventional techniques known to those skilled in the art. [see, for example, "Stereochemistry of Organic Compounds" by E L Eliel (Wiley, New York, 1994).]

The present invention includes all pharmaceutically acceptable isotopically-labelled compounds of Formula (I), (II) or (III) wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^{2}H$ and $^{3}H$, carbon, such as $^{11}C$, $^{13}C$ and $^{14}C$, chlorine, such as $^{36}Cl$, fluorine, such as $^{18}F$, iodine, such as $^{123}I$ and $^{125}I$, nitrogen, such as $^{13}N$ and $^{15}N$, oxygen, such as $^{15}O$, $^{17}O$ and $^{18}O$, phosphorus, such as $^{32}P$, and sulphur, such as $^{35}S$.

Certain isotopically-labelled compounds of Formula (I), (II) or (III), for example, those incorporating a radioactive isotope, are useful in drug and/or substrate tissue distribution studies. The radioactive isotopes tritium, i.e. $^{3}H$, and carbon-14, i.e. $^{14}C$, are particularly useful for this purpose in view of their ease of incorporation and ready means of detection.

Substitution with heavier isotopes such as deuterium, i.e. $^{2}H$, may afford certain therapeutic advantages resulting from greater metabolic stability, for example, increased in vivo half-life or reduced dosage requirements, and hence may be preferred in some circumstances.

Isotopically-labelled compounds of Formula (I), (II) or (III) can generally be prepared by conventional techniques known to those skilled in the art or by processes analogous to those described in the accompanying Examples and Preparations using an appropriate isotopically-labelled reagents in place of the non-labelled reagent previously employed.

The compounds of the present invention may be administered as prodrugs. Thus, certain derivatives of compounds of Formula (I), (II) or (III), which may have little or no pharmacological activity themselves can, when administered into or onto the body, be converted into compounds of Formula (I), (II) or (III) as 'prodrugs'.

Administration of the chemical entities and combinations of entities described herein can be via any of the accepted modes of administration for agents that serve similar utilities including, but not limited to, orally, sublingually, subcutaneously, intravenously, intranasally, topically, transdermally, intraperitoneally, intramuscularly, intrapulmonarilly, vaginally, rectally, or intraocularly. In some embodiments, oral or parenteral administration is used.

Pharmaceutical compositions or formulations include solid, semi-solid, liquid and aerosol dosage forms, such as, e.g., tablets, capsules, powders, liquids, suspensions, suppositories, aerosols or the like. The chemical entities can also be administered in sustained or controlled release dosage forms, including depot injections, osmotic pumps, pills, transdermal (including electrotransport) patches, and the like, for prolonged and/or timed, pulsed administration at a predetermined rate. In certain embodiments, the compositions are provided in unit dosage forms suitable for single administration of a precise dose.

The chemical entities described herein can be administered either alone or more typically in combination with a conventional pharmaceutical carrier, excipient or the like (e.g., mannitol, lactose, starch, magnesium stearate, sodium saccharine, talcum, cellulose, sodium crosscarmellose, glucose, gelatin, sucrose, magnesium carbonate, and the like). If desired, the pharmaceutical composition can also contain minor amounts of nontoxic auxiliary substances such as wetting agents, emulsifying agents, solubilizing agents, pH buffering agents and the like (e.g., sodium acetate, sodium citrate, cyclodextrine derivatives, sorbitan monolaurate, triethanolamine acetate, triethanolamine oleate, and the like). Generally, depending on the intended mode of administration, the pharmaceutical composition will contain about 0.005% to 95%; in certain embodiments, about 0.5% to 50% by weight of a chemical entity. Actual methods of preparing such dosage forms are known, or will be apparent, to those skilled in this art; for example, see *Remington's Pharmaceutical Sciences*, Mack Publishing Company, Easton, Pa.

In certain embodiments, the compositions will take the form of a pill or tablet and thus the composition will contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose, cellulose derivatives or the like. In another solid dosage form, a powder, marume, solution or suspension (e.g., in propylene carbonate, vegetable oils or triglycerides) is encapsulated in a gelatin capsule.

Liquid pharmaceutically administrable compositions can, for example, be prepared by dissolving, dispersing, etc. at least one chemical entity and optional pharmaceutical adjuvants in a carrier (e.g., water, saline, aqueous dextrose, glycerol, glycols, ethanol or the like) to form a solution or suspension. Injectables can be prepared in conventional forms, either as liquid solutions or suspensions, as emulsions, or in solid forms suitable for dissolution or suspension in liquid prior to injection. The percentage of chemical entities contained in such parenteral compositions is highly dependent on the specific nature thereof, as well as the activity of the chemical entities and the needs of the subject. However, percentages of active ingredient of 0.01% to 10% in solution are employable, and will be higher if the composition is a solid which will be subsequently diluted to the above percentages. In certain embodiments, the composition will comprise from about 0.2 to 2% of the active agent in solution.

Pharmaceutical compositions of the chemical entities described herein may also be administered to the respiratory tract as an aerosol or solution for a nebulizer, or as a microfine powder for insufflation, alone or in combination with an inert carrier such as lactose. In such a case, the particles of the pharmaceutical composition have diameters of less than 50 microns, in certain embodiments, less than 10 microns.

In general, the chemical entities provided will be administered in a therapeutically effective amount by any of the accepted modes of administration for agents that serve similar utilities. The actual amount of the chemical entity, i.e., the active ingredient, will depend upon numerous factors such as the severity of the disease to be treated, the age and relative health of the subject, the potency of the chemical entity used the route and form of administration, and other factors. The drug can be administered more than once a day, such as once or twice a day.

In general, the chemical entities will be administered as pharmaceutical compositions by any one of the following routes: oral, systemic (e.g., transdermal, intranasal or by suppository), or parenteral (e.g., intramuscular, intravenous or subcutaneous) administration. In certain embodiments, oral administration with a convenient daily dosage regimen that can be adjusted according to the degree of affliction may be used. Compositions can take the form of tablets, pills, capsules, semisolids, powders, sustained release formulations, solutions, suspensions, elixirs, aerosols, or any other appropriate compositions. Another manner for administering the provided chemical entities is inhalation.

The choice of formulation depends on various factors such as the mode of drug administration and bioavailability of the drug substance. For delivery via inhalation the chemical entity can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes the therapeutic agents (which are formulated in a liquid form) to spray as a mist that is carried into the patient's respiratory tract. MDIs typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the patient's inspiratory air-stream during breathing by the device. In order to achieve a free flowing powder, the therapeutic agent is formulated with an excipient such as lactose. A measured amount of the therapeutic agent is stored in a capsule form and is dispensed with each actuation.

Recently, pharmaceutical compositions have been developed for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a cross-linked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, at least one chemical entity described herein in combination with at least one pharmaceutically acceptable excipient. Acceptable excipients are non-toxic, aid administration, and do not adversely affect the therapeutic benefit of the at least one chemical entity described herein. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Liquid carriers, for injectable solutions, include water, saline, aqueous dextrose, and glycols.

Compressed gases may be used to disperse a chemical entity described herein in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The amount of the chemical entity in a composition can vary within the full range employed by those skilled in the art. Typically, the composition will contain, on a weight percent (wt %) basis, from about 0.01-99.99 wt % of at least one chemical entity described herein based on the total composition, with the balance being one or more suitable pharmaceutical excipients. In certain embodiments, the at least one chemical entity described herein is present at a level of about 1-80 wt %.

In various embodiments, pharmaceutical compositions of the present invention encompass compounds of Formula (I), (II) or (III), salts thereof, and combinations of the above.

Synthetic Methods

The methods of synthesis for the provided chemical entities employ readily available starting materials using the following general methods and procedures. It will be appreciated that where typical or preferred process conditions (i.e., reaction temperatures, times, mole ratios of reactants, solvents, pressures, etc.) are given; other process conditions can also be used unless otherwise stated. Optimum reaction conditions may vary with the particular reactants or solvent used, but such conditions can be determined by one skilled in the art by routine optimization procedures.

Additionally, the methods of this invention may employ protecting groups which prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, Protecting Groups in Organic Synthesis, Third Edition, Wiley, New York, 1999, and references cited therein.

Furthermore, the provided chemical entities may contain one or more chiral centers and such compounds can be prepared or isolated as pure stereoisomers, i.e., as individual enantiomers or diastereomers, or as stereoisomer-enriched mixtures. All such stereoisomers (and enriched mixtures) are included within the scope of this specification, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Ernka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989).

Unless specified to the contrary, the reactions described herein take place at atmospheric pressure, generally within a temperature range from −78° C. to 200° C. Further, except as employed in the Examples or as otherwise specified, reaction times and conditions are intended to be approximate, e.g., taking place at about atmospheric pressure within a temperature range of about −78° C. to about 110° C. over a period of about 1 to about 24 hours; reactions left to run overnight average a period of about 16 hours.

The terms "solvent," "organic solvent," and "inert solvent" each mean a solvent inert under the conditions of the reaction being described in conjunction therewith, including, for example, benzene, toluene, acetonitrile, tetrahydrofuranyl ("THF"), dimethylformamide ("DMF"), chloroform, methylene chloride (or dichloromethane), diethyl ether, methanol, N-methylpyrrolidone ("NMP"), pyridine and the like.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples herein below. However, other equivalent separation or isolation procedures can also be used.

When desired, the (R)- and (S)-isomers may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

EXAMPLES

The following examples serve to more fully describe the manner of making and using the above-described invention. It is understood that these examples in no way serve to limit the true scope of the invention, but rather are presented for illustrative purposes. In the examples below and the synthetic schemes above, the following abbreviations have the following meanings. If an abbreviation is not defined, it has its generally accepted meaning.

aq.=Aqueous
μL=Microliters
μM=Micromolar
NMR=nuclear magnetic resonance
Boc=tert-butoxycarbonyl
Br=Broad
Cbz=Benzyloxycarbonyl
D=Doublet
Δ=chemical shift
° C.=degrees celcius
DCM=Dichloromethane
Dd=doublet of doublets
DMEM=Dulbeco's Modified Eagle's Medium
DMF=N,N-dimethylformamide
DMSO=Dimethylsulfoxide
EtOAc=ethyl acetate
G=Gram
h or hr=Hours
HCV=hepatitus C virus
HPLC=high performance liquid chromatography
Hz=Hertz
IU=International Units
$IC_{50}$=inhibitory concentration at 50% inhibition
J=coupling constant (given in Hz unless otherwise indicated)
M=Multiplet
M=Molar
$M+H^+$=parent mass spectrum peak plus $H^+$
Mg=Milligram
Min=Minutes
mL=Milliliter
mM=Millimolar
Mmol=Millimole
MS=mass spectrum
Nm=Nanomolar
Ppm=parts per million
q.s.=sufficient amount
S=Singlet
RT=room temperature
sat.=Saturated
T=Triplet
TFA=trifluoroacetic acid Equipment Description $^1$H NMR spectra were recorded on a Varian spectrometer. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), quint (quintet), m (multiplet), br (broad).

The analytical low-resolution mass spectra (MS) were recorded on Waters (Acquity). The following conditions were employed described below.

MS Conditions:
Instrument: Waters SQD
Serial Number: F06SQD018N
Scan Mode: Alternating Positive/Negative Electrospray
Scan Range: 125-1200 amu
Scan Time: 150 msec
Interscan Delay: 50 msec
Lc Conditions:
The UPLC analysis was conducted on a Phenomenex Kinetex 1.7 um
2.1×50 mm XB-C18 column at 40° C.
0.2 uL of sample was injected using PLNO (partial loop with needle overfill) injection mode.
The gradient employed was:
Mobile Phase A: Water+0.2% v/v Formic Acid
Mobile Phase B: Acetonitrile+0.15% v/v Formic Acid

| Time | % A | % B | Flow Rate |
|---|---|---|---|
| 0.00 min | 95 | 5 | 1 ml/min |
| 1.1 min | 1 | 99 | 1 ml/min |
| 1.5 min | 1 | 99 | 1 ml/min |

UV detection provided by summed absorbance signal from 210 to 350 nm scanning at 40 Hz.

Schemes and Experimental Procedures

The following schemes and procedures illustrate how compounds of the present invention can be prepared. The specific solvents and reaction conditions referred to are also illustrative and are not intended to be limiting. Compounds not described are either commercially available or are readily prepared by one skilled in the art using available starting materials. The Examples disclosed herein are for illustrative purposes only and are not intended to limit the scope of the invention.

This in no way is meant to limit the scope of the invention or utility of the compounds of Formula (I), (II) or (III). Additional examples contained within were determined to have the shown configuration by spectroscopic methods well known to those skilled in the art including, but not limited to, 1D and 2D NMR methods, vibrational circular dichroism and X-ray crystallography.

TABLE 3

Compounds

| Example No. | Parent Structure | Chemical Name |
|---|---|---|
| 1 | | 1-((5-((5-(4-chlorophenyl)furo[2,3-d]pyrimidin-4-yl)thio)-1,3,4-oxadiazol-2-yl)methyl)pyrrolidin-2-one |
| 2 | | 1-((5-((5-(4-chlorophenyl)furo[2,3-d]pyrimidin-4-yl)thio)-1,3,4-oxadiazol-2-yl)methyl)pyrrolidin-2-one |
| 3 | | 1-((5-((5-(4-chlorophenyl)furo[2,3-d]pyrimidin-4-yl)thio)-1,3,4-oxadiazol-2-yl)methyl)pyrrolidin-2-one |

TABLE 3-continued

| Compounds | | |
|---|---|---|
| Example No. | Parent Structure | Chemical Name |
| 4 | | 1-((5-((5-(furan-2-yl)furo[2,3-d]pyrimidin-4-yl)thio)-1,3,4-oxadiazol-2-yl)methyl)pyrrolidin-2-one |
| 5 | | 1-((5-((5-(furan-2-yl)furo[2,3-d]pyrimidin-4-yl)thio)-1,3,4-oxadiazol-2-yl)methyl)pyrrolidin-2-one |
| 6 | | 1-((5-((5-(thiophen-2-yl)furo[2,3-d]pyrimidin-4-yl)thio)-1,3,4-oxadiazol-2-yl)methyl)pyrrolidin-2-one |
| 7 | | 1-((5-((5-(5-methylthiophen-2-yl)furo[2,3-d]pyrimidin-4-yl)thio)-1,3,4-oxadiazol-2-yl)methyl)pyrrolidin-2-one |

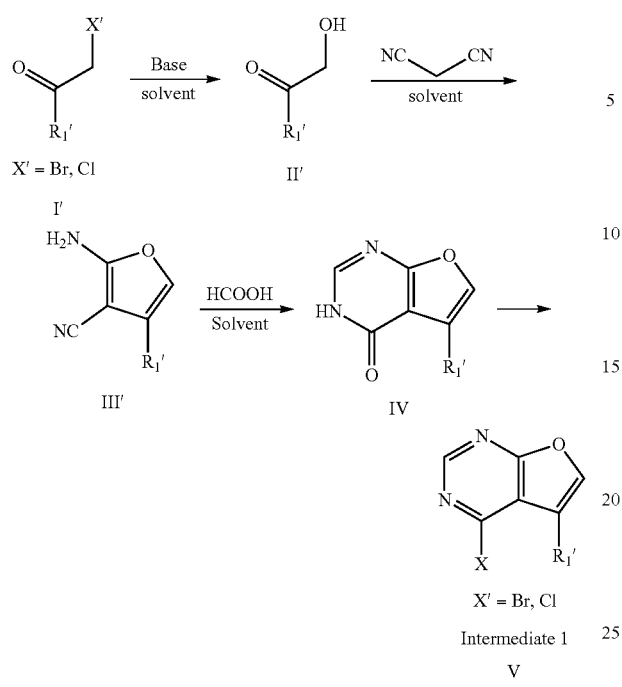

$R_1'$: substituted and non-substituted aryl

As a first step, α-halo ketone (I') can be reacted with a suitable base such as HCOONa, CH₃COONa, NaOH in a suitable solvent or a mixture of solvents such as EtOH, MeOH, water, DMF at elevated temperature such as 60-150° C. for a certain length of reaction time ranging from 3 minutes to 12 hours to prepare the corresponding α-hydroxy ketone (II'). As a second step, α-hydroxy ketone (I') can be reacted with malononitrile using a base such as diethylamine, triethylamine, diisopropylethylamine, pyridine to make a compound (III'). At this time, the reaction can be performed using DMF or the like, as a solvent which does not adversely affect the reaction. Furthermore, the reaction is performed at, but not limited thereto room temperature or an elevated temperature. The reaction time can range from minutes to hours. As a third step, the compound (III') may be reacted with HCOOH to form a compound (IV). The reaction can be performed using Ac₂O or the like, such as an organic solvent which does not adversely affect the reaction and performed at room temperature or under heating. As a fourth step, the compound (IV) may react in a phosphorous oxychloride solution to prepare a compound (V). At this time, pentachlorophosphine or phenyldiethylamine may be added thereto to perform the reaction. The reaction can be conducted without using any solvent or with a solvent, which does not adversely affect the reaction, such as DMF. Furthermore, the reaction is preferably conducted, but not limited thereto, under heat.

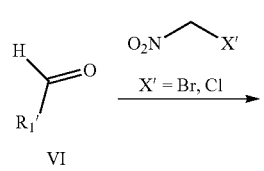

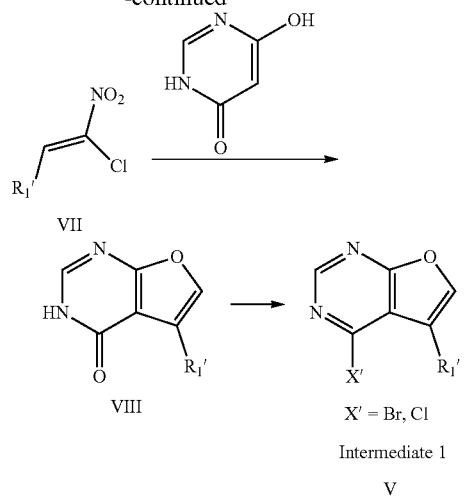

An optionally substituted aldehyde (VI), such as furan-2-carbaldehyde, can be reacted with bromonitromethane or chloronitromethane under basic conditions in a suitable solvent to provide the chloro-nitro olefin (VII). The reaction may be performed using xylenes, toluene or the like, as an organic solvent which is does not adversely affect the reaction and performed preferably under heating. Some additives, such as KF as a catalytic amount, are preferred to promote the reaction. Compound (VII) can then be reacted with dihydroxypyrimidine in the presence of a suitable base, such as DBU, using MeOH, EtOH, or the like, as a solvent which does not adversely affect the reaction. Furthermore, the reaction is preferably conducted, but not limited thereto, under heat to provide compound (VIII). At the third step, compound (VIII) can react in a phosphorous oxychloride solution to provide compound (V). At this time, pentachlorophosphine or phenyldiethylamine may be added thereto to perform the reaction. The reaction can be conducted without using any solvent or with a solvent, which is believed to not adversely affect the reaction, such as DMF. Furthermore, the reaction is preferably conducted, but not limited thereto, under heat.

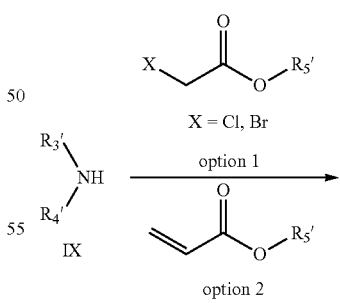

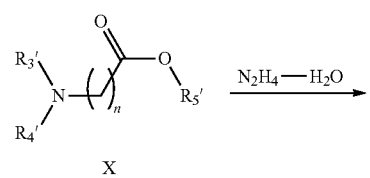

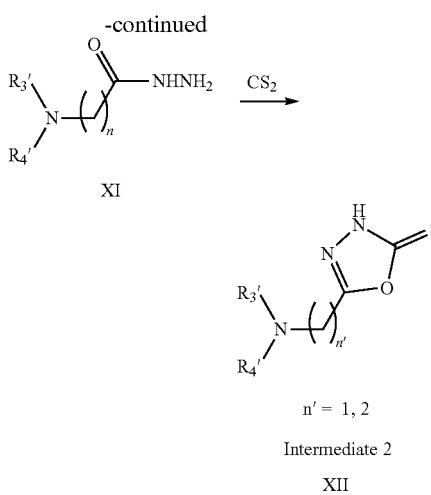

n' = 1, 2

Intermediate 2

XI

An optionally substituted amine (IX) is reacted to α-halo ester as option 1 using a base such as $K_2CO_3$, NaH, in a suitable solvent such as toluene, DMF, to prepare a compound (X) with n=1. An optionally substituted amine (IX) can also be reacted to an acrylate ester in the presence of $ZrCl_4$ in a suitable solvent such as DCM to provide compound (X) with n=2. Furthermore, the reaction is performed, but not limited thereto at room temperature or at elevated temperature. Compound (X) can then be reacted with hydrazine monohydrate using MeOH, EtOH, or the like, as a solvent which does not adversely affect the reaction. Furthermore, the reaction is preferably conducted, but not limited thereto, under heating to provide compound (XI). At the third step, compound (XI) can be reacted with carbon disulfide in the presence of a suitable base, such as $K_2CO_3$, $Na_2CO_3$, $Cs_2CO_3$, and using MeOH, EtOH, water or the like, as a solvent which does not adversely affect the reaction. Furthermore, the reaction is performed, but not limited thereto at room temperature or at elevated temperature to provide compound (XII).

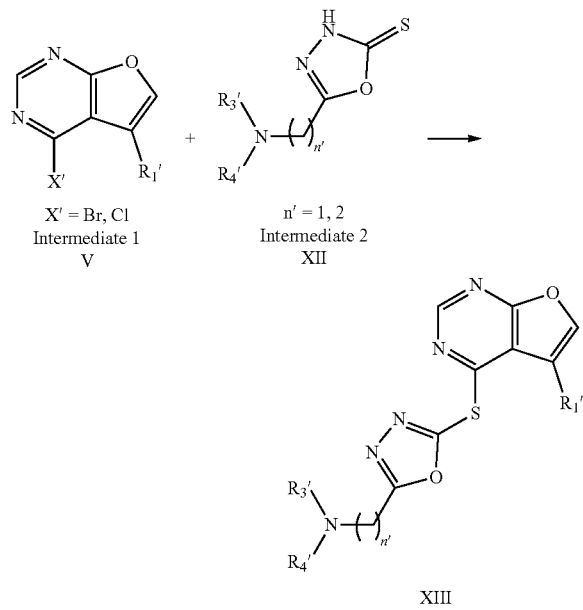

wherein $R_1'$ is a 5- or 6-membered aryl or heteroaryl that may be optionally substituted, $R_3'$ and $R_4'$ are independently alkyl or together form a 5-membered cycloalkyl that may be optionally substituted by-chloro, fluoro, oxo or alkoxy.

Intermediate 1 (V), which may be prepared according to the description above, is reacted with Intermediate 2 (XII) which may be prepared according to the description above using a suitable base such as diethylamine, triethylamine, diisopropylethylamine, pyridine in a suitable solvent or a mixture of solvents such as DME, DMF at elevated temperature such as 60-150° C. for a certain length of reaction time ranging from 2 hours to 24 hours to prepare the corresponding final compound (XII).

Example 1

Intermediate 1: 4-chloro-5-(4-chlorophenyl)furo[2,3-d]pyrimidine

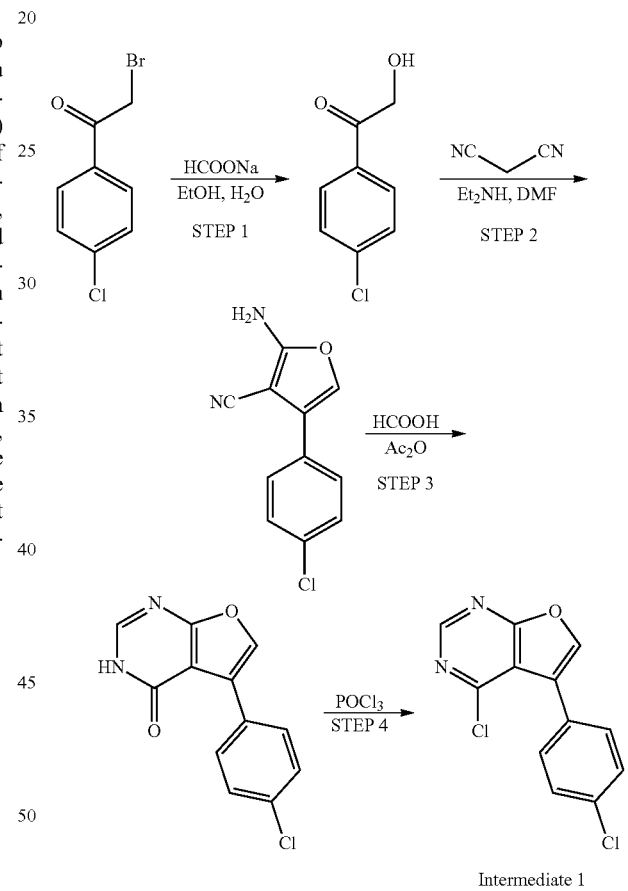

STEP 1: A solution of 2-bromo-1-(4-chlorophenyl)ethanone (12 g) and HCOONa (20.94 g) in EtOH (90 mL) and $H_2O$ (16 mL) was heated at 150° C. for 5 minutes by microwave. After cooling down to room temperature, the suspension was partitioned between EtOAc and water. The organic layer was washed with brine, dried over $Na_2SO_4$, and concentrated down to give the crude product which was purified by column chromatography (silica gel: 30-100% EtOAc in petroleum ether) to provide 1-(4-chlorophenyl)-2-hydroxyethanone (8 g, LC/MS (ESI): m/z (M, M+2)= 171.03, 173.02, yield=92%).

STEP 2: A solution of 1-(4-chlorophenyl)-2-hydroxyethanone (8 g), malononitrile (3.1 g), and $Et_2NH$ (1.7 g) in DMF (20 mL) was stirred at room temperature for 2 hours. After water was added to the reaction, the precipitate was collected by filtration to provide 2-amino-4-(4-chlorophenyl)furan-3-carbonitrile (8.2 g, LC/MS (ESI): m/z (M, M+2)= 219.07, 221.09, yield=80%) as a white solid.

STEP 3: A solution of 2-amino-4-(4-chlorophenyl)furan-3-carbonitrile (8 g) in HCOOH (40 mL) and Ac$_2$O (40 mL) was heated at 125° C. and stirred overnight under N$_2$. After cooling down to room temperature, the solvents were removed under reduced pressure to give the crude product (LC/MS (ESI): m/z (M, M+2)=247.23, 249.21), which was used in next step without further purification.

STEP 4: A solution of 5-(4-chlorophenyl)furo[2,3-d]pyrimidin-4(3H)-one (c.a. 8 g from the previous step) in POCl$_3$ (40 mL) was heated to 100° C. and stirred overnight under N$_2$. After cooling down to room temperature, the solvents were removed by evaporation under reduced pressure to give the crude product, which was purified by column chromatography (silica gel: 0-30% EtOAc in petroleum ether) to provide 4-chloro-5-(4-chlorophenyl)furo[2,3-d]pyrimidine (intermediate 1, 2.3 g, LC/MS (ESI): m/z (M, M+2)=265.04, 267.06, yield=23%).

Example 2

Intermediate 2: 1((5-thioxo-4,5-dihydro-1,3,4-oxadiazol-2-yl) methyl)pyrrolidin-2-one

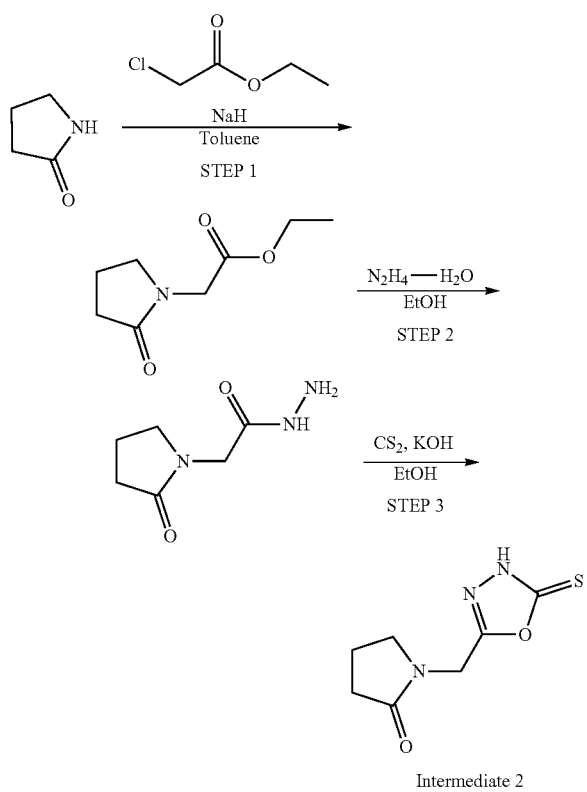

STEP 1: To a solution of pyrrolidin-2-one (10 g) in toluene (100 mL) was added NaH (5.5 g) portionwise at 0° C. under N$_2$. The suspension was stirred for 30 minutes and ethyl 2-chloroacetate (15.8 g) was added by a syringe. The reaction was then heated to 110° C. and stirred overnight under N$_2$. After adding 1 N HCl to quench the reaction, it was partitioned between EtOAc and water. The organic layer was washed with brine, dried over Na$_2$SO$_4$, and concentrated down to give the crude product, which was purified by column chromatography (silica gel: 0-50% EtOAc in petroleum ether) to afford ethyl 2-(2-oxopyrrolidin-1-yl)acetate (9 g, LC/MS (ESI): m/z (M+1)=172.08, yield=45%).

STEP 2: A solution of ethyl 2-(2-oxopyrrolidin-1-yl)acetate (9 g) and hydrazine monohydrate (5.26 g) in EtOH (90 mL) was heated to 100° C. and stirred overnight under N$_2$. After cooling down to room temperature, the solvents were removed by evaporation under reduced pressure to give the crude product, which was used in the next step without further purification (c.a. 8 g, LC/MS (ESI): m/z (M+1)=158.12, yield=96%).

STEP 3: Carbon disulfide (11.7 g) was slowly added to a suspension of 2-(2-oxopyrrolidin-1-yl)acetohydrazide (c.a. 8 g) and potassium hydroxide (2.85 g) in EtOH (200 mL). The reaction mixture was refluxed for 12 hours. Upon completion, the solvent was removed under reduced pressure and the residue partitioned between EtOAc and 1N HCl. The organic layer was washed with brine, dried over Na$_2$SO$_4$, and concentrated down to give the crude product, which was purified by column chromatography (silica gel: 0-10% MeOH in dichloromethane) to afford 1-((5-thioxo-4,5-dihydro-1,3,4-oxadiazol-2-yl)methyl)pyrrolidin-2-one (intermediate 2-1 g, LC/MS (ESI): m/z (M+1)=200.19).

Example 3

1-((5-((5-(4-chlorophenyl)furo[2,3-d]pyrimidin-4-yl)thio)-1,3,4-oxadiazol-2-yl)methyl)pyrrolidin-2-one

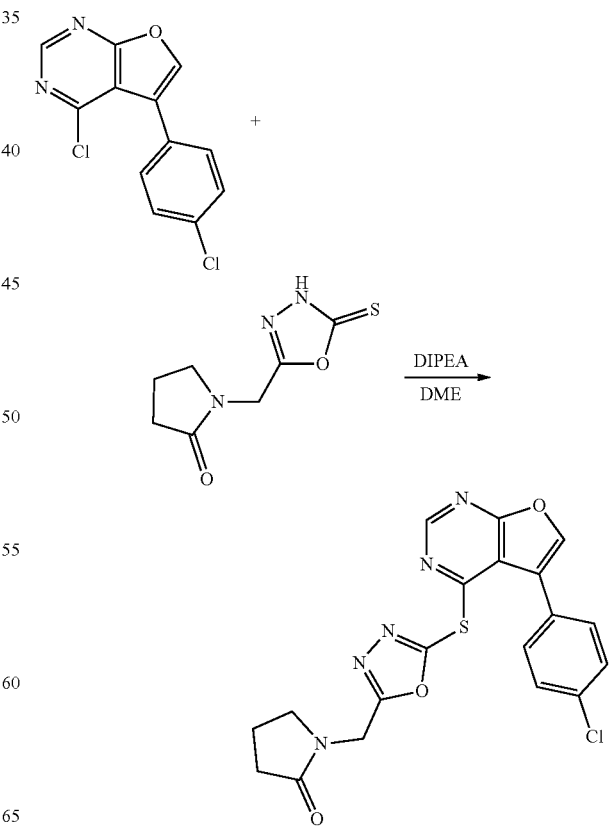

A solution of 4-chloro-5-(4-chlorophenyl)furo[2,3-d]pyrimidine (intermediate 1, 30 mg), 1-((5-thioxo-4,5-dihydro-1,3,4-oxadiazol-2-yl)methyl)pyrrolidin-2-one (intermediate 2, 24.8 mg), and N,N-diisopropylethylamine (21.9 mg) in dimethoxyethane (2 mL) was heated up to 120° C., and stirred overnight under $N_2$. After cooling down to room temperature, it was partitioned between EtOAc and water. The organic layer was washed with brine, dried over $Na_2SO_4$, and concentrated down to give the crude product which was purified by HPLC Gilson (C18, 40-100 MeCN in water with 0.1% formic acid) to afford 1-((5-((5-(4-chlorophenyl)furo[2,3-d]pyrimidin-4-yl)thio)-1,3,4-oxadiazol-2-yl)methyl)pyrrolidin-2-one (13 mg, LC/MS (ESI): m/z (M, M+2)=428.12, 430.1, yield=26.8%). 1H NMR (400 MHz, CDCl$_3$) δ ppm 8.65 (s, 1H), 7.74 (s, 1H), 7.53-7.45 (m, 4H), 4.79 (s, 2H), 3.57-3.47 (m, 2H), 2.44 (t, J=8.1 Hz, 2H), 2.16-2.05 (m, 2H).

Example 4

1-((5-((5-(4-chlorophenyl)furo[2,3-d]pyrimidin-4-yl)thio)-1,3,4-oxadiazol-2-yl)methyl)pyrrolidin-2-one

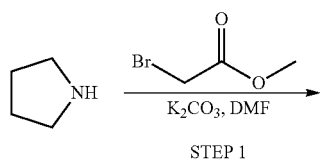

STEP 1

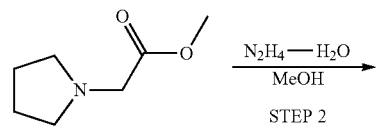

STEP 2

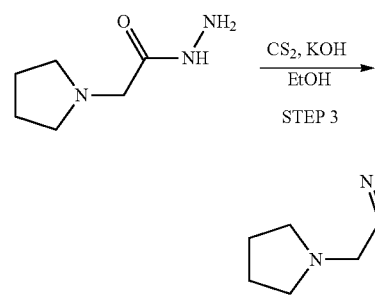

STEP 3

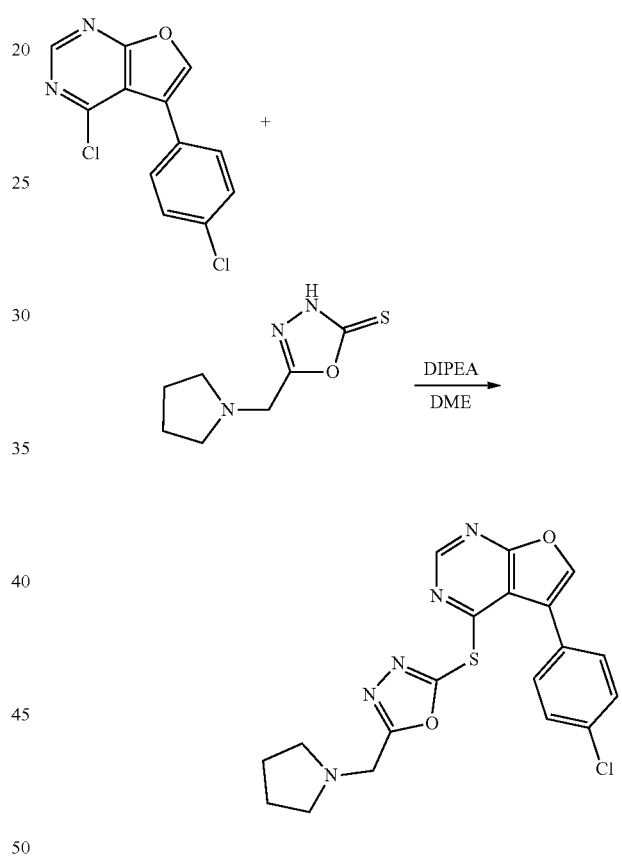

STEP 1: To a solution of pyrrolidine (5 g) and methyl 2-bromoacetate (11.8 g) in DMF (150 mL) was added $K_2CO_3$ (5.5 g) at room temperature. The suspension was further stirred overnight. The reaction mixture was then partitioned between ether and water. The aqueous layer was extracted three times, and the combined organic layer was washed with brine, dried over $Na_2SO_4$, and concentrated down to give the product (4 g, LC/MS (ESI): m/z (M+1)= 144.13, yield=33%).

STEP 2: A solution of methyl 2-(pyrrolidin-1-yl)acetate (2 g) and hydrazine monohydrate (15 mL) in MeOH (50 mL) was refluxed overnight. After cooling down to room temperature, the solvents were removed by evaporation under reduced pressure to give the crude product, which was used in the next step without further purification (c.a. 2 g, LC/MS (ESI): m/z (M+1)=144.21).

STEP 3: Carbon disulfide (266 mg) was slowly added to a suspension of 2-(pyrrolidin-1-yl)acetohydrazide (500 mg) and potassium hydroxide (196 mg) in EtOH (1.4 mL). The reaction mixture was refluxed for 12 hours. Upon completion, the reaction mixture was poured into ice-water and the pH was adjusted to approximately 7. The solvent was then removed under reduced pressure and the residue was purified by column chromatography (silica gel: 0-10% MeOH in dichloromethane) to afford 5-(pyrrolidin-1-ylmethyl)-1,3,4-oxadiazole-2(3H)-thione (128 mg, LC/MS (ESI): m/z (M+1)= 186.19).

A solution of 4-chloro-5-(4-chlorophenyl)furo[2,3-d]pyrimidine (intermediate 1, 30 mg), 5-(pyrrolidin-1-ylmethyl)-1,3,4-oxadiazole-2(3H)-thione (23.1 mg), and N,N-diisopropylethylamine (21.9 mg) in dimethoxyethane (2 mL) was heated up to 120° C., and stirred 4 hours. After cooling down to room temperature, it was partitioned between DCM and water. The aqueous layer was extracted three times, and the combined organic layer was washed with brine, dried over $Na_2SO_4$, and concentrated down to give the crude product which was purified by HPLC Gilson (C18, 30-100 MeCN in water with 0.1% formic acid) to afford 1-((5-((5-(4-chlorophenyl)furo[2,3-d]pyrimidin-4-yl)thio)-1,3,4-oxadiazol-2-yl)methyl)pyrrolidin-2-one (8 mg, LC/MS (ESI): m/z (M, M+2)=414.1, 416.08, yield=17%). 1H NMR (400 MHz, CDCl$_3$) δ ppm 8.73 (s, 1H), 8.46 (s, 1H), 7.72-7.60 (m, 4H), 3.96 (s, 2H), 2.59-2.52 (m, 4H), 1.76-1.63 (m, 4H).

Example 5

1-((5-((5-(4-chlorophenyl)furo[2,3-d]pyrimidin-4-yl)thio)-1,3,4-oxadiazol-2-yl)methyl)pyrrolidin-2-one

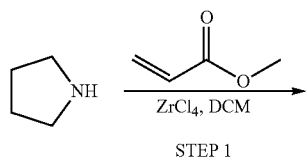

STEP 1

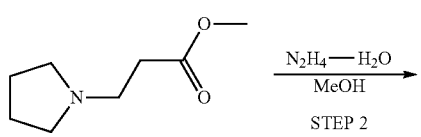

STEP 2

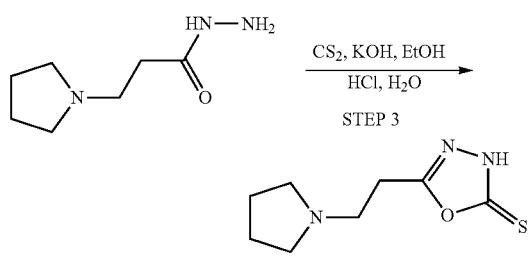

STEP 3

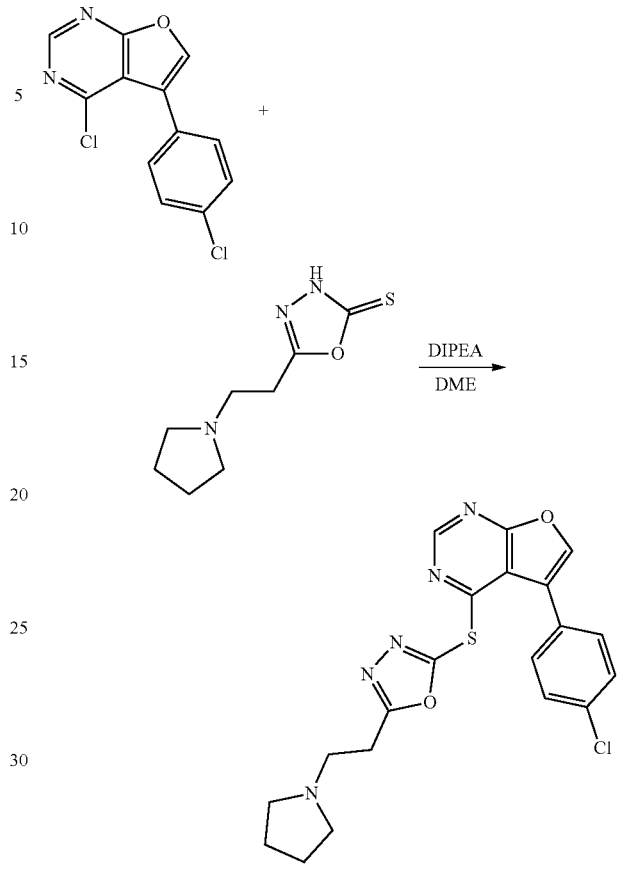

STEP 1: A mixture of pyrrolidine (3.22 g), methyl acrylate (4.65 g), and zirconium (IV) chloride (1.05 g) in anhydrous DCM (80 mL) was stirred at room temperature for 1 hour. The reaction was quenched with water and the organic layer was separated. The aqueous layer was extracted three times, and the combined organic layer was washed with brine, dried over $Na_2SO_4$, and concentrated down to give the crude product which was used in the next step without further purification (4 g, LC/MS (ESI): m/z (M+1)=158.24, yield=56%).

STEP 2: A solution of methyl 3-(pyrrolidin-1-yl)propanoate (2 g) and hydrazine monohydrate (15 mL) in MeOH (50 mL) was refluxed overnight. After cooling down to room temperature, the solvents were removed by evaporation under reduced pressure to give the crude product, which was used in the next step without further purification (LC/MS (ESI): m/z (M+1)=158.25).

STEP 3: To a solution of 3-(pyrrolidin-1-yl)propanehydrazide (500 mg) in EtOH (5 mL) was added carbon disulfide (727 mg) followed by potassium hydroxide (357 mg in 1.5 mL water) at room temperature. The reaction mixture was stirred at room temperature overnight. Upon completion, the reaction mixture was filtered, and the precipitate was washed with EtOH. The filtrate was concentrated down to give the crude product, which was purified by column chromatography (silica gel: 0-20% MeOH in dichloromethane) to provide 5-(2-(pyrrolidin-1-yl)ethyl)-1,3,4-oxadiazole-2(3H)-thione (170 mg, LC/MS (ESI): m/z (M+1)= 200.19).

A solution of 4-chloro-5-(4-chlorophenyl)furo[2,3-d]pyrimidine (intermediate 1, 100 mg), 5-(2-(pyrrolidin-1-yl)ethyl)-1,3,4-oxadiazole-2(3H)-thione (83 mg), and N,N-diisopropylethylamine (98 uL) in dimethoxyethane (2 mL) was heated up to 120° C., and stirred 4 hours. After cooling down to room temperature, it was partitioned between DCM and water. The aqueous layer was extracted three times, and the combined organic layer was washed with brine, dried over $Na_2SO_4$, and concentrated down to give the crude product which was purified by HPLC Gilson (C18, 30-100 MeCN in water with 0.1% formic acid) to afford 1-((5-((5-(4-chlorophenyl)furo[2,3-d]pyrimidin-4-yl)thio)-1,3,4-oxadiazol-2-yl)methyl)pyrrolidin-2-one (15 mg, LC/MS (ESI): m/z (M, M+2)=428.26, 430.23, yield=10%). 1H NMR (400 MHz, $CDCl_3$) δ ppm 8.74 (s, 1H), 8.47 (s, 1H), 7.70-7.61 (m, 4H), 3.31 (t, J=7.1 Hz, 2H), 2.90 (t, J=6.6 Hz, 2H), 2.62-2.52 (m, 4H), 1.74-1.64 (m, 4H).

Example 6

1-((5-((5-(furan-2-yl)furo[2,3-d]pyrimidin-4-yl)thio)-1,3,4-oxadiazol-2-yl)methyl)pyrrolidin-2-one

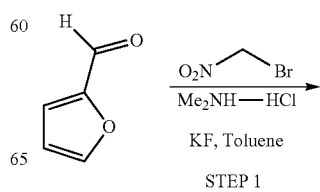

STEP 1

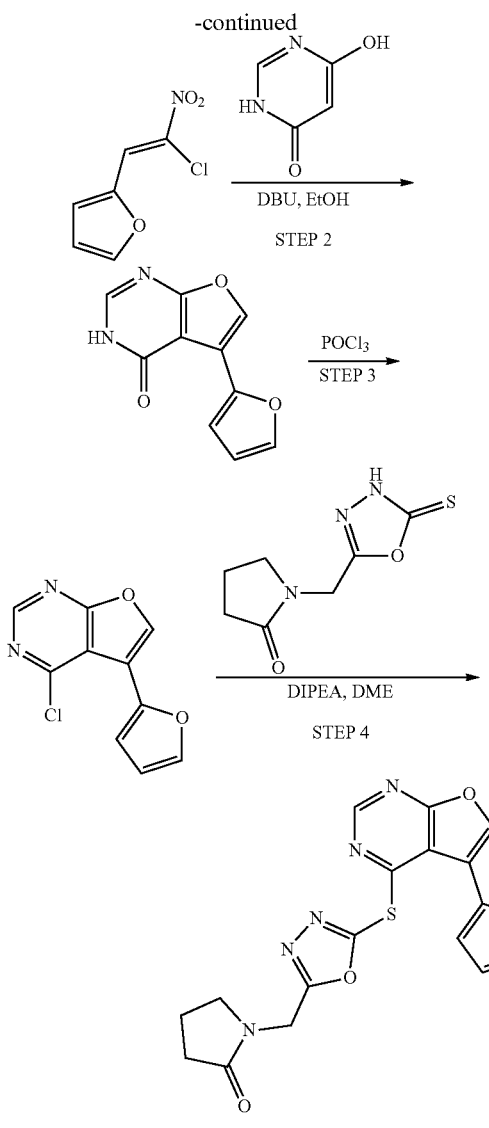

for 1 hour under $N_2$. After cooling down to room temperature, the solvent was removed and the residue was partitioned between DCM and saturated $NaHCO_3$. The organic layer was separated, washed with brine, dried over $Na_2SO_4$, and concentrated down to give the crude product which was purified by column chromatography (silica gel: 0-30% EtOAc in petroleum ether) to provide 4-chloro-5-(furan-2-yl)furo[2,3-d]pyrimidine (200 mg).

STEP 4: A solution of 4-chloro-5-(furan-2-yl)furo[2,3-d]pyrimidine (50 mg), 1-((5-thioxo-4,5-dihydro-1,3,4-oxadiazol-2-yl)methyl)pyrrolidin-2-one (intermediate 2, 68 mg), and N,N-diisopropylethylamine (79 uL) in dimethoxyethane (1.5 mL) was heated up to 120° C., and stirred 6 hours under $N_2$. After cooling down to room temperature, it was partitioned between EtOAc and water. The organic layer was washed with brine, dried over $Na_2SO_4$, and concentrated down to give the crude product which was purified by HPLC Gilson (C18, 40-100 MeCN in water with 0.1% formic acid) to provide 1-((5-((5-(furan-2-yl)furo[2,3-d]pyrimidin-4-yl)thio)-1,3,4-oxadiazol-2-yl)methyl)pyrrolidin-2-one (20 mg, LC/MS (ESI): m/z (M+1)=384.42, yield=23%). 1H NMR (400 MHz, DMSO-d6) δ ppm 8.76 (s, 1H), 8.67 (s, 1H), 7.97 (d, J=1.2 Hz, 1H), 6.96 (d, J=3.3 Hz, 1H), 6.73 (dd, J=3.3, 1.9 Hz, 1H), 4.78 (s, 2H), 3.41 (t, J=7.0 Hz, 2H), 2.28 (t, J=8.1 Hz, 2H), 2.02-1.91 (m, 2H).

Example 7

1-((5-((5-(furan-2-yl)furo[2,3-d]pyrimidin-4-yl)thio)-1,3,4-oxadiazol-2-yl)methyl)pyrrolidin-2-one

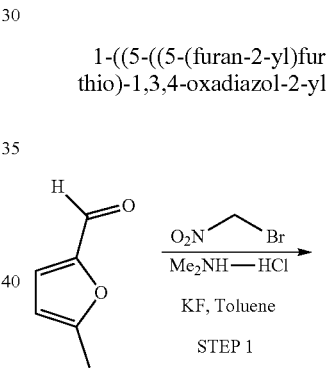

STEP 1: A mixture of furan-2-carbaldehyde (500 mg), bromonitromethane (1.38 g), dimethylamine hydrochloride (3.8 g), and KF (46 mg) in toluene (10 mL) was heated to 110° C. and this was stirred overnight. The reaction mixture was filtered to remove the solid. The filtrate was diluted with EtOAc, and the organic layer was washed with brine, dried over $Na_2SO_4$, and concentrated down to give the crude product which was purified by column chromatography (silica gel: 0-10% EtOAc in petroleum ether) to provide 2-(2-chloro-2-nitrovinyl)furan (810 mg).

STEP 2: To a solution of 2-(2-chloro-2-nitrovinyl)furan (810 mg), 6-hydroxypyrimidin-4(3H)-one (523 mg) in EtOH (10 mL) was added DBU (1.42 g) and the resulting mixture was refluxed overnight. After cooling down to the room temperature, the solvent was removed and the residue was partitioned between EtOAc and water. The organic layer was washed with brine, dried over $Na_2SO_4$, and concentrated down to give the crude product which was purified by column chromatography (silica gel: 0-30% EtOAc in petroleum ether) to provide 5-(furan-2-yl)furo[2,3-d]pyrimidin-4(3H)-one (270 mg).

STEP 3: A solution of 5-(furan-2-yl)furo[2,3-d]pyrimidin-4(3H)-one (270 mg) in $POCl_3$ (8 mL) was heated at 110° C.

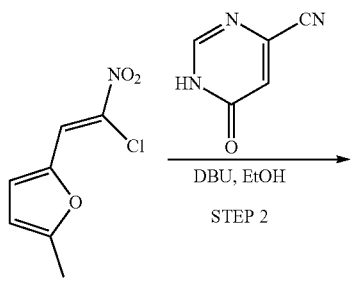

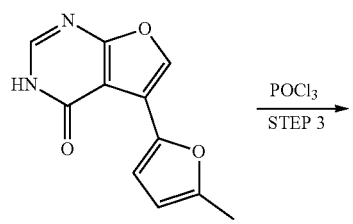

-continued

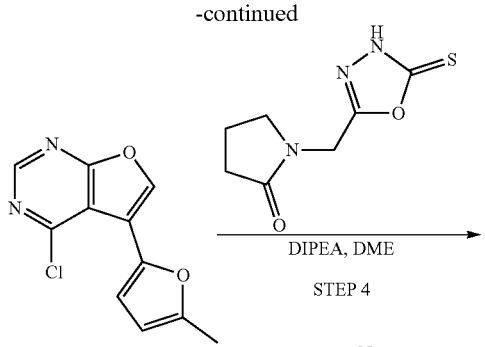

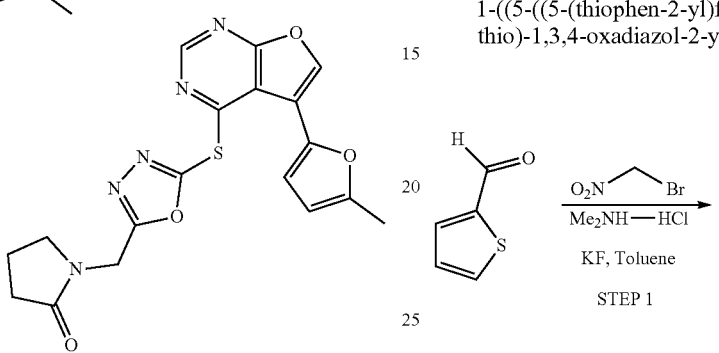

STEP 1: A mixture of 5-methylfuran-2-carbaldehyde (400 mg), bromonitromethane (966 mg), dimethyamine hydrochloride (2.67 g), and KF (32 mg) in toluene (10 mL) was heated to 110° C. and this was stirred overnight. The reaction mixture was filtered to remove the solid. The filtrate was diluted with EtOAc, and the organic layer was washed with brine, dried over $Na_2SO_4$, and concentrated down to give the crude product which was purified by column chromatography (silica gel: 0-10% EtOAc in petroleum ether) to provide 2-(2-chloro-2-nitrovinyl)-5-methylfuran (510 mg).

STEP 2: To a solution of 2-(2-chloro-2-nitrovinyl)-5-methylfuran (510 mg), 6-hydroxypyrimidin-4(3H)-one (305 mg) in EtOH (8 mL) was added DBU (828 mg) and the resulting mixture was refluxed overnight. After cooling down to the room temperature, the solvent was removed and the residue was partitioned between EtOAc and water. The organic layer was washed with brine, dried over $Na_2SO_4$, and concentrated down to give the crude product which was purified by column chromatography (silica gel: 0-30% EtOAc in petroleum ether) to afford 5-(5-methylfuran-2-yl)furo[2,3-d]pyrimidin-4(3H)-one (210 mg).

STEP 3: A solution of 5-(5-methylfuran-2-yl)furo[2,3-d]pyrimidin-4(3H)-one (210 mg) in $POCl_3$ (8 mL) was heated at 110° C. for 1 hour under $N_2$. After cooling down to room temperature, the solvent was removed and the residue was partitioned between DCM and saturated $NaHCO_3$. The organic layer was separated, washed with brine, dried over $Na_2SO_4$, and concentrated down to give the crude product which was purified by column chromatography (silica gel: 0-20% EtOAc in petroleum ether) to afford 4-chloro-5-(5-methylfuran-2-yl)furo[2,3-d]pyrimidine (184 mg).

STEP 4: A solution of 4-chloro-5-(5-methylfuran-2-yl)furo[2,3-d]pyrimidine (50 mg), 1-((5-thioxo-4,5-dihydro-1,3,4-oxadiazol-2-yl)methyl)pyrrolidin-2-one (intermediate 2, 64 mg), and N,N-diisopropylethylamine (74 uL) in dimethoxyethane (1.5 mL) was heated up to 120° C., and stirred 6 hours under $N_2$. After cooling down to room temperature, it was partitioned between EtOAc and water. The organic layer was washed with brine, dried over $Na_2SO_4$, and concentrated down to give the crude product which was purified by HPLC Gilson (C18, 40-100 MeCN in water with 0.1% formic acid) to afford 1-((5-((5-(furan-2-yl)furo[2,3-d]pyrimidin-4-yl)thio)-1,3,4-oxadiazol-2-yl)methyl)pyrrolidin-2-one (20 mg, LC/MS (ESI): m/z (M+1)=398.51, yield=24%). 1H NMR (400 MHz, DMSO-d6) δ ppm 8.74 (s, 1H), 8.61 (s, 1H), 6.81 (d, J=3.1 Hz, 1H), 6.32 (d, J=2.2 Hz, 1H), 4.78 (s, 2H), 3.46-3.39 (m, 2H), 2.42 (s, 3H), 2.28 (t, J=8.0 Hz, 2H), 2.08-1.92 (m, 2H).

Example 8

1-((5-((5-(thiophen-2-yl)furo[2,3-d]pyrimidin-4-yl)thio)-1,3,4-oxadiazol-2-yl)methyl)pyrrolidin-2-one

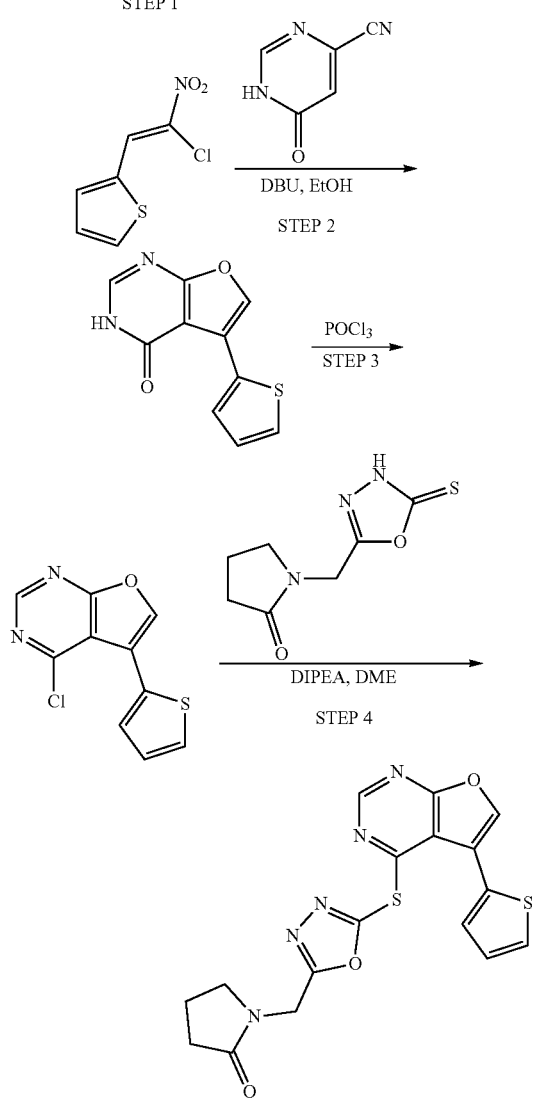

STEP 1: A mixture of thiophene-2-carbaldehyde (1 g), bromonitromethane (2.37 g), dimethylamine hydrochloride (6.5 g), and KF (88 mg) in xylenes (25 mL) was heated to 125° C. and this was stirred overnight. The reaction mixture was filtered to remove the solid. The filtrate was diluted with EtOAc, and the organic layer was washed with brine, dried over $Na_2SO_4$, and concentrated down to give the crude product which was purified by column chromatography (silica gel: 0-10% EtOAc in petroleum ether) to provide 2-(2-chloro-2-nitrovinyl)thiophene (2.5 g).

STEP 2: To a solution of 2-(2-chloro-2-nitrovinyl)thiophene (500 mg), 6-hydroxypyrimidin-4(3H)-one (295 mg) in EtOH (5 mL) was added DBU (803 mg) and the resulting mixture was refluxed overnight. After cooling down to the room temperature, the solvent was removed and the residue was partitioned between EtOAc and water. The organic layer was washed with brine, dried over $Na_2SO_4$, and concentrated down to give the crude product which was purified by column chromatography (silica gel: 0-50% EtOAc in petroleum ether) to provide 5-(thiophen-2-yl)furo[2,3-d]pyrimidin-4(3H)-one (145 mg).

STEP 3: A solution of 5-(thiophen-2-yl)furo[2,3-d]pyrimidin-4(3H)-one (140 mg) in $POCl_3$ (3 mL) was heated at 110° C. for 2 hours under $N_2$. After cooling down to room temperature, the solvent was removed and the residue was partitioned between DCM and saturated $NaHCO_3$. The organic layer was separated, washed with brine, dried over $Na_2SO_4$, and concentrated down to give the crude product which was purified by column chromatography (silica gel: 0-20% EtOAc in petroleum ether) to afford 4-chloro-5-(thiophen-2-yl)furo[2,3-d]pyrimidine (100 mg).

STEP 4: A solution of 4-chloro-5-(thiophen-2-yl)furo[2,3-d]pyrimidine (30 mg), 1-((5-thioxo-4,5-dihydro-1,3,4-oxadiazol-2-yl)methyl)pyrrolidin-2-one (intermediate 2, 30 mg), and N,N-diisopropylethylamine (24.5 mg) in dimethoxyethane (1.0 mL) was heated up to 125° C., and stirred 5 hours under $N_2$. After cooling down to room temperature, it was partitioned between EtOAc and water. The organic layer was washed with brine, dried over $Na_2SO_4$, and concentrated down to give the crude product which was purified by HPLC Gilson (C18, 30-100 MeCN in water with 0.1% formic acid) to afford 1-((5-((5-(thiophen-2-yl)furo[2,3-d]pyrimidin-4-yl)thio)-1,3,4-oxadiazol-2-yl)methyl)pyrrolidin-2-one (13 mg, LC/MS (ESI): m/z (M+1)=400.43, yield=25%). 1H NMR (400 MHz, DMSO-d6) δ ppm 8.76 (s, 1H), 8.53 (s, 1H), 7.79 (dd, J=5.1, 1.2 Hz, 1H), 7.46 (dd, J=3.5, 1.2 Hz, 1H), 7.28 (dd, J=5.1, 3.5 Hz, 1H), 4.76 (s, 2H), 3.39 (t, J=7.0 Hz, 2H), 2.27 (t, J=8.1 Hz, 2H), 2.03-1.91 (m, 2H).

Example 9

1-((5-((5-(5-methylthiophen-2-yl)furo[2,3-d]pyrimidin-4-yl)thio)-1,3,4-oxadiazol-2-yl)methyl)pyrrolidin-2-one

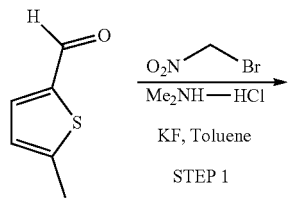

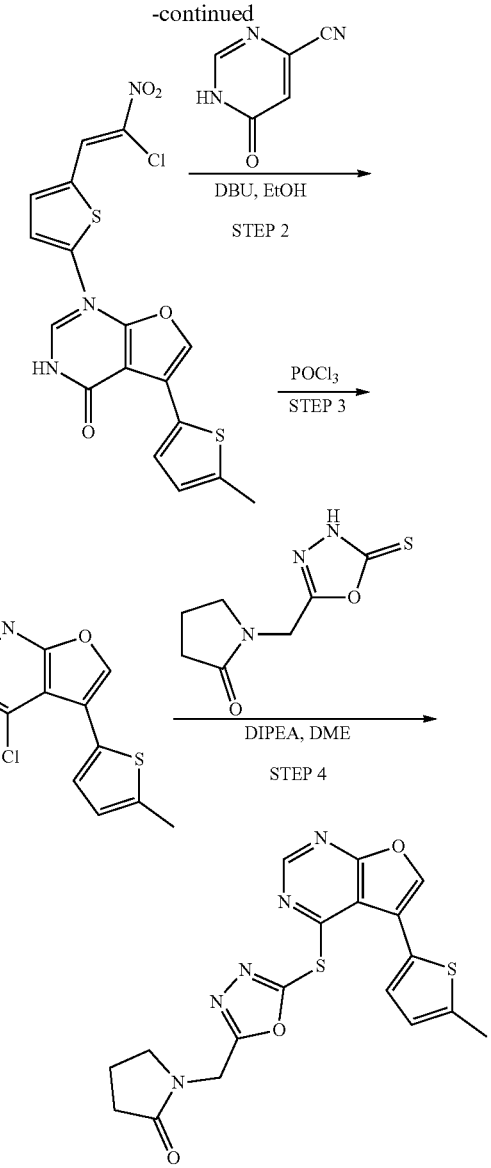

STEP 1: A mixture of 5-methylthiophene-2-carbaldehyde (1 g), bromonitromethane (2.1 g), dimethylamine hydrochloride (5.8 g), and KF (78 mg) in xylenes (12 mL) was heated to 125° C. and stirred overnight. The reaction mixture was filtered to remove the solid. The filtrate was diluted with EtOAc, and the organic layer was washed with brine, dried over $Na_2SO_4$, and concentrated down to give the crude product which was purified by column chromatography (silica gel: 0-10% EtOAc in petroleum ether) to provide 2-(2-chloro-2-nitrovinyl)-5-methylthiophene (1.1 g).

STEP 2: To a solution of 2-(2-chloro-2-nitrovinyl)-5-methylthiophene (580 mg), 6-hydroxypyrimidin-4(3H)-one (319 mg) in EtOH (6 mL) was added DBU (867 mg) and the resulting mixture was refluxed overnight. After cooling down to room temperature, the solvent was removed and the residue was partitioned between EtOAc and water. The organic layer was washed with brine, dried over $Na_2SO_4$, and concentrated down to give the crude product which was purified by column chromatography (silica gel: 0-50% EtOAc in petroleum ether) to provide 5-(5-methylthiophen-2-yl)furo[2,3-d]pyrimidin-4(3H)-one (130 mg).

STEP 3: A solution of 5-(5-methylthiophen-2-yl)furo[2,3-d]pyrimidin-4(3H)-one (130 mg) in POCl₃ (3 mL) was heated at 110° C. for 2 hours under N₂. After cooling down to room temperature, the solvent was removed and the residue was partitioned between DCM and saturated NaHCO₃. The organic layer was separated, washed with brine, dried over Na₂SO₄, and concentrated down to give the crude product which was purified by column chromatography (silica gel: 0-20% EtOAc in petroleum ether) to provide 4-chloro-5-(5-methylthiophen-2-yl)furo[2,3-d]pyrimidine (120 mg).

STEP 4: A solution of 4-chloro-5-(5-methylthiophen-2-yl)furo[2,3-d]pyrimidine (30 mg), 1-((5-thioxo-4,5-dihydro-1,3,4-oxadiazol-2-yl)methyl)pyrrolidin-2-one (intermediate 2, 28.6 mg), and N,N-diisopropylethylamine (23.1 mg) in dimethoxyethane (1.0 mL) was heated up to 125° C., and stirred 5 hours under N₂. After cooling down to room temperature, it was partitioned between EtOAc and water. The organic layer was washed with brine, dried over Na₂SO₄, and concentrated down to give the crude product which was purified by HPLC Gilson (C18, 30-100 MeCN in water with 0.1% formic acid) to provide 1-((5-((5-(5-methylthiophen-2-yl)furo[2,3-d]pyrimidin-4-yl)thio)-1,3,4-oxadiazol-2-yl)methyl)pyrrolidin-2-one (18 mg, LC/MS (ESI): m/z (M+1)=414.45, yield=36%). 1H NMR (400 MHz, DMSO-d6) δ ppm 8.74 (s, 1H), 8.47 (s, 1H), 7.24 (d, J=3.5 Hz, 1H), 7.00-6.92 (m, 1H), 4.76 (s, 2H), 3.39 (t, J=7.0 Hz, 2H), 2.53 (d, J=0.8 Hz, 3H), 2.27 (t, J=8.1 Hz, 2H), 2.02-1.93 (m, 2H).

HIV Latency Disruption Assays

For the Jurkat HIV Latency assay, compounds were dissolved and titrated in DMSO and diluted 100-fold in assay medium (RPMI-1640 containing 10% fetal bovine serum) containing an equal mixture of three HIV-infected Jurkat cell clones (C16, 115 and N6) at a total concentration of 1-2×10⁵ cells/mL. To test stability, compounds are pre-incubated in assay medium for 48 hours at 37° C. prior to adding cells (48 hr EC50). Compounds that induce HIV expression result in a dose-dependent production of the HIV expressed luciferase enzyme. After the incubation of cells with compound for 24 hours at 37° C., HIV activation and cytotoxicity are determined by measuring luminescence after the addition of Promega Steady-Glo® Luciferase Assay reagent or CellTiter-Glo® Luminescent Cell Viability Assay reagent, respectively.

Potency results from the above assay are set forth in Table 4.

TABLE 4

Averaged potency of invention compounds for HIV latency disruption in Jurkat HIV cells.

| Example No. | Jurkat Mean PXC50 |
|---|---|
| 1 | 6.199 |
| 2 | 5.990 |
| 3 | 6.137 |
| 4 | 6.309 |
| 5 | — |
| 6 | 6.045 |
| 7 | 6.204 |

For the PBMC cytotoxicity assay, compounds are dissolved and titrated in DMSO and diluted 100-fold in assay medium (RPMI-1640 containing 10% fetal bovine serum) containing peripheral blood mononuclear cells (PBMCs) from healthy donors at a concentration of 4×10⁵ cells/mL. After the incubation of PBMCs with compound for 72 hours at 37° C., cytotoxicity is determined by measuring luminescence after the addition of Promega CellTiter-Glo® Luminescent Cell Viability Assay reagent.

For the assessment of compound activity in primary patient cells, PBMCs were obtained by continuous-flow leukapheresis from HIV-infected, antiretrovirally-treated, aviremic patients whose plasma HIV-1 RNA was less than 50 copies/mL at the time of collection. PBMCs were isolated by Ficoll-Hypaque density gradient centrifugation and cryopreserved in the vapor phase of liquid nitrogen. On the day of assay, cells were rapidly thawed to room temperature in a 37° C. water bath and total CD4+ T cells were isolated by negative selection (Stemcell Technologies). CD4+ T cells were reconstituted in assay medium (RPMI-1640 containing 10% fetal bovine serum, 10 ug/mL Fuzeon® and 200 nM Rilpivirin) and 5×10⁶ were plated onto 2 mL 96-well polypropylene plates. Compounds were dissolved in DMSO, diluted 1:250 into assay medium and then titrated into assay medium supplemented with 0.4% DMSO with a minimum of 3 biological replicates per each treatment condition. Compound titrations were transferred to the cells and the assay plates were incubated at 37° C. for 24 hours. Following incubation, the assay plates were centrifuged at 400×g for 10 minutes and the cell-free supernatants were removed and discarded. The nucleic acid from the cell pellets were extracted, purified and segregated into RNA and DNA components using AllPrep DNA/RNA 96-well kits (Qiagen). HIV reactivation was quantified from the RNA fraction by one-step RT-qPCR (applied Biosystems) using primers and probe that target gag messenger RNA. HIV copies were calculated based on extrapolations from standard curves generated with known quantities of synthetic target HIV gag DNA in the same PCR reaction plate as the samples. A minimum of 3 technical RT-qPCR replicates were run for each biological replicate.

Data were normalized and modeled accordingly raw data were used to calculate the absolute number of HIV-gag RNA copies per million CD4+ T cells, with the value for each compound and concentration based on the averaged value of 3 to 5 biological replicates, with each biological replicate value being the average of 3 technical RT-qPCR replicates.

The dose-response curve was fit to an unconstrained four parameter logistic equation, defined as:

$$y = V_{max}\{1-[x^n \div (K^n + x^n)]\} + Y_2$$

Where:
x=compound concentration
y=normalized response data
$V_{max}$=upper bound of response
K=EC₅₀
$Y_2$=lower bound or baseline of response
n=hill coefficient An example of dose-response HIV latency disruption in vitro is presented in FIG. 1 comparing the compound of invention (Example-1) to the compound of prior art (Compound-A) in peripheral blood CD4+ T cells from a HIV-infected fully-suppressed subject. Value of cell-associated HIV gag RNA (caRNA) per million CD4+ T cells are averaged from 3 biological replicates (3 technical replicates each) are presented for each tested concentration of +/− Standard Error Mean, and dose-response curves are derived by 4-parameter logistic regression (Example-1: plain line, Compound_A: dotted line). As shown in FIG. 1, the compound of the invention (Example-1) displays increased potency (EC50=47 nM) relative to the compound of the prior art (Compound-A, EC50=308 nM) in this example.

Compound A

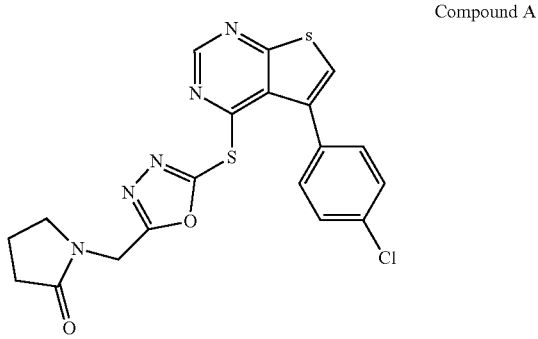

Average potencies derived from the above assay from multiple donors are summarized in Table 5 for Example 1-5 and 7 (pEC50).

TABLE 5

| Example No. | CD4 Mean PXC50 |
| --- | --- |
| 1 | 7.447 |
| 2 | 6.959 |
| 3 | 6.959 |
| 4 | 7.824 |
| 5 | 7.398 |
| 6 | — |
| 7 | 6.409 |

Table 4. Averaged potency of invention compounds for HIV latency disruption in CD4+ T cells from HIV-infected donors Table 4. Averaged potency of invention compounds for HIV latency disruption in CD4+ cells from HIV-infected donors

What is claimed is:

1. A compound of the formula (I):

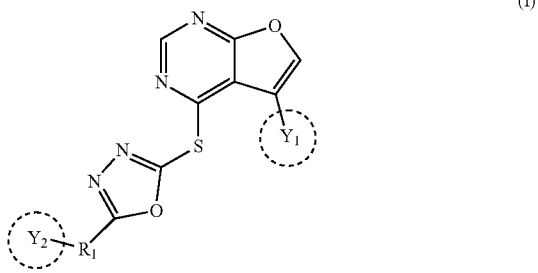

(I)

wherein:

$Y_1$ is a 5- or 6-membered aryl or heteroaryl optionally substituted by one or more substituents independently selected from the group consisting of chloro, fluoro, oxo, and alkoxy;

$R_1$ is $C_1$-$C_6$ alkylene; and $Y_2$ is a ring of the formula:

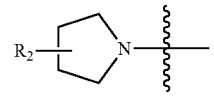

wherein $R_2$ is selected from the group consisting of -chloro, fluoro, oxo and alkoxy;

or a pharmaceutically acceptable salt thereof.

2. The compound according to claim 1, wherein $Y_1$ is an aryl.

3. The compound according to claim 2, wherein $Y_1$ is an aryl substituted by Cl.

4. The compound according to claim 3, wherein $Y_1$ is of the formula:

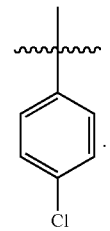

5. The compound according to claim 1, wherein Y1 is a 5-membered heteroaryl.

6. The compound according to claim 5, wherein the 5-membered heteroaryl contains at least one heteroatom which is O or S.

7. The compound according to claim 1, wherein $R_1$ is $C_1$ alkyl.

8. The compound according to claim 1, wherein $R_1$ is $C_2$ alkyl.

9. The compound according to claim 1, selected from the group consisting of:

| Parent Structure | Chemical Name |
| --- | --- |
|  | 1-((5-((5-(4-chlorophenyl)furo[2,3-d]pyrimidin-4-yl)thio)-1,3,4-oxadiazol-2-yl)methyl)pyrrolidin-2-one |

| Parent Structure | Chemical Name |
|---|---|
| | 1-((5-((5-(4-chlorophenyl)furo[2,3-d]pyrimidin-4-yl)thio)-1,3,4-oxadiazol-2-yl)methyl)pyrrolidin-2-one |
| | 1-((5-((5-(4-chlorophenyl)furo[2,3-d]pyrimidin-4-yl)thio)-1,3,4-oxadiazol-2-yl)methyl)pyrrolidin-2-one |
| | 1-((5-((5-(furan-2-yl)furo[2,3-d]pyrimidin-4-yl)thio)-1,3,4-oxadiazol-2-yl)methyl)pyrrolidin-2-one |

| Parent Structure | Chemical Name |
|---|---|
| 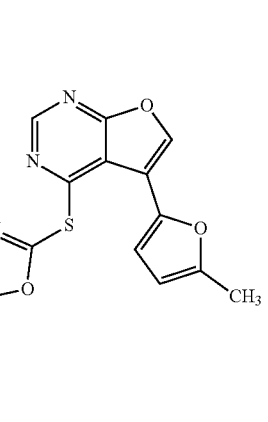 | 1-((5-((5-(furan-2-yl)furo[2,3-d]pyrimidin-4-yl)thio)-1,3,4-oxadiazol-2-yl)methyl)pyrrolidin-2-one |
| 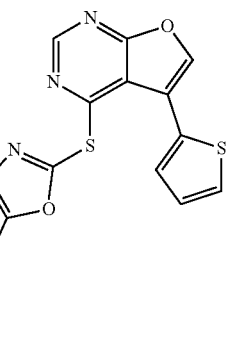 | 1-((5-((5-(thiophen-2-yl)furo[2,3-d]pyrimidin-4-yl)thio)-1,3,4-oxadiazol-2-yl)methyl)pyrrolidin-2-one |
| 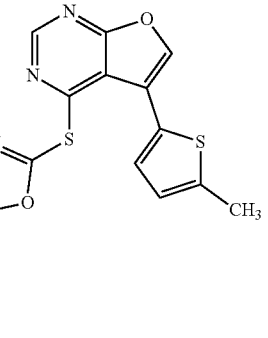 | 1-((5-((5-(5-methylthiophen-2-yl)furo[2,3-d]pyrimidin-4-yl)thio)-1,3,4-oxadiazol-2-yl)methyl)pyrrolidin-2-one |
and a pharmaceutically acceptable salt thereof.

10. A compound of the formula (II):

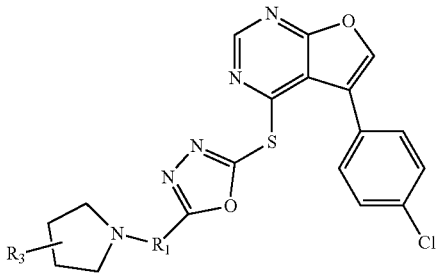

(II)

wherein $R_1$ is $C_1$-$C_6$ alkyl; and
$R_3$ is hydrogen, oxo, chloro or fluoro.

11. A compound of the formula (III):

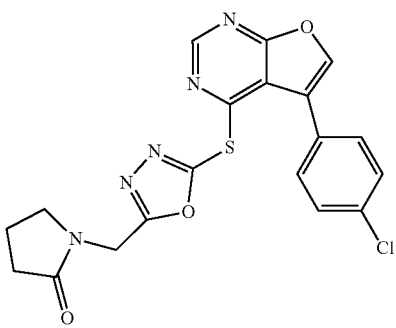

(III)

or a pharmaceutically acceptable salt thereof.

12. A pharmaceutical composition comprising a compound according to claim 1, or a pharmaceutically acceptable salt thereof, and a pharmaceutically acceptable excipient.

13. The composition of claim 12, wherein the compound is present in an amorphous form.

14. The composition of claim 12, wherein the composition is in a tablet form.

15. The composition of claim 12, wherein the compound is present as a spray dried dispersion.

16. A method of curing an HIV infection in a subject comprising administering to the subject a compound of claim 1, or a pharmaceutically acceptable salt thereof.

17. A method of treating an HIV infection in a subject comprising administering to the subject a compound of claim 1, or a pharmaceutically acceptable salt thereof.

18. A method of preventing an HIV infection in a subject at risk for developing an HIV infection, comprising administering to the subject a compound of claim 1, or a pharmaceutically acceptable salt thereof.

* * * * *